United States Patent
Pereira et al.

(10) Patent No.: US 7,288,120 B2
(45) Date of Patent: Oct. 30, 2007

(54) SYNTHESIS OF TETRAAZAPENTAMETHINE COMPOUNDS, AND PROCESSES FOR DYEING KERATIN FIBERS USING THIS SYNTHESIS

(75) Inventors: Rui Pereira, Bussy Saint Georges (FR); Hervé Burgaud, Damartin en Goele (FR)

(73) Assignee: L'Oreal S.A., Paris (FR)

( * ) Notice: Subject to any disclaimer, the term of this patent is extended or adjusted under 35 U.S.C. 154(b) by 275 days.

(21) Appl. No.: 11/009,058

(22) Filed: Dec. 13, 2004

(65) Prior Publication Data

US 2005/0198744 A1   Sep. 15, 2005

Related U.S. Application Data

(60) Provisional application No. 60/532,939, filed on Dec. 30, 2003.

(30) Foreign Application Priority Data

Dec. 12, 2003  (FR) .................................. 03 14655

(51) Int. Cl.
*A61K 7/13* (2006.01)
(52) U.S. Cl. ........................ 8/405; 8/407; 8/565; 8/567; 8/568; 8/570; 8/571; 8/572; 8/573; 8/574; 8/654; 8/655; 546/184; 548/318.1; 548/400; 132/202; 132/208

(58) Field of Classification Search .................... 8/405, 8/407, 565, 567, 568, 570, 571, 572, 573, 8/574, 654, 655; 546/184; 548/318.1, 400; 132/202, 208
See application file for complete search history.

(56) References Cited

U.S. PATENT DOCUMENTS

| 3,173,905 A | 3/1965 | Sureau et al. | |
| 2004/0127692 A1* | 7/2004 | David et al. | ................. 534/605 |

FOREIGN PATENT DOCUMENTS

| EP | 1 378 544 | 1/2004 |
| FR | 1 291 555 | 4/1962 |

OTHER PUBLICATIONS

STIC Search Report dated Dec. 29, 2006.*
Huenig S. et al., "Tetraaza-Pentamethinfarbstoffe" Justus Liebigs Annalen Der chemie, Verlag Chemie GMBH, Weinheim, DE, vol. 667, 1963, pp. 72-85, XP002237035.
English language Derwent Abstract of EP 1 378 544, Jan. 7, 2004.

* cited by examiner

*Primary Examiner*—Eisa Elhilo
(74) *Attorney, Agent, or Firm*—Finnegan, Henderson, Farabow, Garrett & Dunner

(57) ABSTRACT

The present disclosure relates to processes for synthesizing tetraazapentamethine compounds that comprise reacting at least one compound of azine type with at least one oxidizing agent. The disclosure also relates to processes for dyeing keratin fibers, for example human keratin fibers, that comprise using such synthetic processes.

17 Claims, No Drawings

SYNTHESIS OF TETRAAZAPENTAMETHINE COMPOUNDS, AND PROCESSES FOR DYEING KERATIN FIBERS USING THIS SYNTHESIS

This application claims benefit of U.S. Provisional Application No. 60/532,939, filed Dec. 30, 2003.

The present disclosure relates to the field of dyeing keratin fibers. For example, the disclosure relates to processes for preparing tetraazapentamethine compounds from the corresponding azines, and to processes for dyeing keratin fibers in which the processes for preparing these compounds are used.

It is known practice to dye keratin fibers, for instance human keratin fibers such as the hair, with dye compositions containing direct dyes. Direct dyes are colored and coloring molecules that have affinity for the fibers. Dye compositions are applied to the fibers, left to act for a time sufficient to obtain a suitable degree of coloration, and the fibers are then generally rinsed.

The direct dyes that are conventionally used include nitrobenzene, anthraquinone, nitropyridine, azo, xanthene, acridine, azine and triarylmethane.

The use of direct dyes makes it possible to obtain chromatic colorations. However, these colorations are only temporary or semi-permanent, as a result of the nature of the bonds between the direct dyes and the keratin fiber. These interactions cause the desorption of the dyes from the surface and/or from the core of the fiber to take place relatively easily.

The colorations also generally show low dyeing strength, and do not sufficiently withstand washing and perspiration.

In addition, these direct dyes are generally light-sensitive, because of the chromophore's low resistance to photochemical attack. As a result, coloration of the hair fades over time.

In addition, the light sensitivity of these dyes depends on their uniform distribution or their distribution as aggregates in and/or on the keratin fiber.

There may also be problems of stability of the direct dye in the dye composition itself, which lead to a change in color of the dye and also to poor storage of the dye composition.

One object of the present disclosure is to solve the above problems.

In one aspect, the disclosure relates to processes for preparing tetraazapentamethine compounds of formula (I):

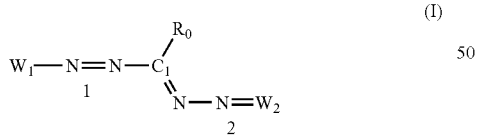
(I)

wherein
   $W_1$ is chosen from cationic heteroaromatic radicals of formulae (II) and (III):

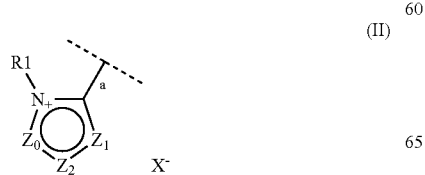
(II)

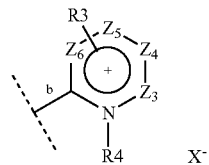
(III)

$W_2$ is chosen from heteroaromatic radicals of formulae (IV) and (V):

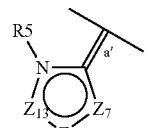
(IV)

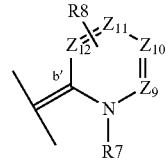
(V)

wherein, in formulae (II), (III), (IV) and (V):
- $Z_0$ is chosen from $CR_2$ radicals, nitrogen, and $NR_{21}$ radicals,
- $Z_1$ is chosen from oxygen, sulfur, and $NR_9$ radicals,
- $Z_2$ is chosen from nitrogen and $CR_{10}$ radicals,
- $Z_3$ is chosen from nitrogen and $CR_{11}$ radicals,
- $Z_4$ is chosen from nitrogen and $CR_{12}$ radicals,
- $Z_5$ is chosen from nitrogen and $CR_{13}$ radicals,
- $Z_6$ is chosen from nitrogen and $CR_{14}$ radicals,
- $Z_7$ is chosen from oxygen, sulfur, and $NR_{15}$ radicals,
- $Z_8$ is chosen from nitrogen and $CR_{16}$ radicals,
- $Z_9$ is chosen from nitrogen and $CR_{17}$ radicals,
- $Z_{10}$ is chosen from nitrogen and $CR_{18}$ radicals,
- $Z_{11}$ is chosen from nitrogen and $CR_{19}$ radicals,
- $Z_{12}$ is chosen from nitrogen and $CR_{20}$ radicals,
- $Z_{13}$ is chosen from $CR_6$ radicals, nitrogen, and $NR_{22}$ radicals,
- each of the rings of formulae (II), (III), (IV) and (V) comprises not more than three nitrogen atoms, two of which may be contiguous,
- bond a of the 5-membered cationic heteroaromatic radical of formula (II) is linked to the nitrogen atom $N_1$ of formula (I),
- bond b of the 6-membered cationic heteroaromatic radical of formula (III) is linked to the nitrogen atom $N_1$ of formula (I),
- double bond a' of the 5-membered heteroaromatic radical of formula (IV) is linked to the nitrogen atom $N_2$ of formula (I),
- double bond b' of the 6-membered heteroaromatic radical of formula (V) is linked to the nitrogen atom $N_2$ of formula (I),
- bond b, linking the cationic heteroaromatic radical of formula (III) to the nitrogen atom $N_1$ of formula (I), is in an ortho or para position relative to the nitrogen atom bearing the radical $R_4$ when $Z_5$ is chosen from CR$_{13}$ radicals, and in an ortho position relative to the nitrogen atom bearing the radical R$_4$ when Z$_5$ is nitrogen, bond b', linking the heteroaromatic radical of formula (V) to the nitrogen atom N$_2$ of formula (I), is in an ortho or para position relative to the nitrogen atom bearing the radical R$_7$ when Z$_{11}$ is chosen from CR$_{19}$ radicals, and in an ortho position relative to the nitrogen atom bearing the radical R$_7$ when Z$_{11}$ is nitrogen, R$_2$, R$_6$, R$_{10}$ and R$_{16}$, which may be identical or different, are chosen from hydrogen; linear and branched C$_1$-C$_4$ alkyl radicals that are unsubstituted or substituted with one to three substituents chosen from hydroxyl, C$_1$-C$_2$ alkoxy, C$_2$-C$_4$ (poly)hydroxyalkoxy, amino, C$_1$-C$_2$ (di)alkylamino, carboxyl and sulfonic radicals; phenyl radicals that are unsubstituted or substituted with one or two radicals chosen from hydroxyl, C$_1$-C$_2$ alkoxy, C$_2$-C$_4$ (poly)hydroxyalkoxy, amino and C$_1$-C$_2$ (di)alkylamino radicals; carboxyl radicals; and sulfonylamino radicals, R$_1$, R$_4$, R$_5$, R$_7$, R$_9$, R$_{15}$, R$_{21}$ and R$_{22}$, which may be identical or different, are linear or branched C$_1$-C$_8$ alkyl radicals that are unsubstituted or substituted with one to three substituents chosen from hydroxyl, C$_1$-C$_2$ alkoxy, C$_2$-C$_4$ (poly)hydroxyalkoxy, amino, C$_1$-C$_2$ (di)alkylamino, carboxyl and sulfonic radicals;

R$_0$, R$_3$, R$_8$, R$_{11}$, R$_{12}$, R$_{13}$, R$_{14}$, R$_{17}$, R$_{18}$, R$_{19}$ and R$_{20}$, which may be identical or different, are chosen from hydrogen; linear and branched C$_1$-C$_{16}$ hydrocarbon-based chains, wherein the chains are optionally saturated or unsaturated with one to three unsaturations, wherein the chains are unsubstituted or substituted with one to three substituents chosen from hydroxyl, C$_1$-C$_2$ alkoxy, C$_2$-C$_4$ (poly)hydroxyalkoxy, amino, C$_1$-C$_2$ (di)alkylamino, carboxyl, sulfonic, sulfonylamino and C$_2$-C$_4$ (poly)hydroxyalkylamino radicals, and halogen atoms such as chlorine, fluorine and bromine, and wherein the chains may be interrupted by one or two oxygen, nitrogen, or sulfur atoms, or by a SO$_2$ radical; phenyl radicals that are unsubstituted or substituted with one to three substituents chosen from hydroxyl, C$_1$-C$_2$ alkoxy, C$_2$-C$_4$ (poly)hydroxyalkoxy, amino, C$_1$-C$_2$ (di)alkylamino, carboxyl, sulfonic, sulfonylamino and C$_2$-C$_4$ (poly)hydroxyalkylamino radicals, and halogen atoms such as chlorine, fluorine and bromine; and heteroaryl radicals chosen from pyrazolyl, pyrrolyl, imidazolyl, thiazolyl, oxazolyl, triazolyl, pyridyl, pyrimidinyl, triazinyl, pyrazinyl and pyridazinyl radicals, none of R$_0$, R$_3$, R$_8$, R$_{11}$, R$_{12}$, R$_{13}$, R$_{14}$, R$_{17}$, R$_{18}$, R$_{19}$ and R$_{20}$ comprise a peroxide bond, a diazo radical, or a nitroso radical, R$_2$ with R$_{10}$, R$_{11}$ with R$_{12}$, R$_{16}$ with R$_{16}$, and R$_{17}$ with R$_{18}$, which may be identical or different, can form 5- or 6-membered carbon-based aromatic rings that are unsubstituted or substituted with one or two substituents chosen from hydroxyl, amino, (di)(C$_1$-C$_2$)alkylamino, C$_1$-C$_2$ alkoxy and C$_2$-C$_4$ (poly)hydroxyalkylamino radicals, X is chosen from organic and mineral anions.

Processes according to the disclosure comprise reacting, in the presence of at least one oxidizing agent, at least one azine compound of formula (VI) and/or (VII):

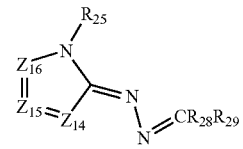

formula (VI)

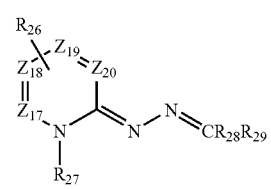

formula (VII)

wherein:

Z$_{14}$ is chosen from oxygen, sulfur, NR$_9$ radicals, and NR$_{15}$ radicals, Z$_{15}$ is chosen from nitrogen, CR$_{10}$ radicals, and CR$_{16}$ radicals, Z$_{16}$ is chosen from CR$_2$ radicals, CR$_6$ radicals, nitrogen, NR$_{21}$ radicals, and NR$_{22}$ radicals, R$_{25}$ is a linear or branched C$_1$-C$_8$ alkyl radical that is unsubstituted or substituted with one to three substituents chosen from hydroxyl, C$_1$-C$_2$ alkoxy, C$_2$-C$_4$ (poly)hydroxyalkoxy, amino, C$_1$-C$_2$ (di)alkylamino, carboxyl and sulfonic radicals, Z$_{17}$ is chosen from nitrogen, CR$_{11}$ radicals, and CR$_{17}$ radicals, Z$_{18}$ is chosen from nitrogen, CR$_{12}$ radicals, and CR$_{18}$ radicals, Z$_{19}$ is chosen from nitrogen, CR$_{13}$ radicals, and CR$_{19}$ radicals, Z$_{20}$ is chosen from nitrogen, CR$_{14}$ radicals, and CR$_{20}$ radicals, R$_{26}$ is chosen from hydrogen; linear and branched C$_1$-C$_{16}$ hydrocarbon-based chains, wherein the chains are optionally saturated or unsaturated with one to three unsaturations, wherein the chains are unsubstituted or substituted with one to three substituents chosen from hydroxyl, C$_1$-C$_2$ alkoxy, C$_2$-C$_4$ (poly)hydroxyalkoxy, amino, C$_1$-C$_2$ (di)alkylamino, carboxyl, sulfonic, sulfonylamino and C$_2$-C$_4$ (poly)hydroxyalkylamino radicals, and halogen atoms such as chlorine, fluorine and bromine, and wherein the chains may be interrupted by one or two oxygen, nitrogen, or sulfur atoms or by an SO$_2$ radical; phenyl radicals that are unsubstituted or substituted with one to three substituents chosen from hydroxyl, C$_1$-C$_2$ alkoxy, C$_2$-C$_4$ (poly)hydroxyalkoxy, amino, C$_1$-C$_2$ (di)alkylamino, carboxyl, sulfonic, sulfonylamino and C$_2$-C$_4$ (poly)hydroxyalkylamino radicals, and halogen atoms such as chlorine, fluorine and bromine; and heteroaryl radicals chosen from pyrazolyl, pyrrolyl, imidazolyl, thiazolyl, oxazolyl, triazolyl, pyridyl, pyrimidinyl, triazinyl, pyrazinyl and pyridazinyl radicals, R$_{27}$ is a linear or branched C$_1$-C$_8$ alkyl radical that is unsubstituted or substituted with one to three substituents chosen from hydroxyl, C$_1$-C$_2$ alkoxy, C$_2$-C$_4$ (poly)hydroxyalkoxy, amino, C$_1$-C$_2$ (di)alkylamino, carboxyl and sulfonic radicals R$_{28}$ and R$_{29}$, which may be identical or different, are chosen from hydrogen; C$_1$-C$_6$ alkyl radicals, such as C$_1$-C$_4$ alkyl radicals; and linear and branched C$_1$-C$_6$ alkoxy radicals, such as $C_1$-$C_4$ alkoxy radicals, and are chosen such that at least one of the two radicals is not hydrogen.

Another aspect of the present disclosure relates to processes for dyeing keratin fibers, such as human keratin fibers, comprising applying to wet or dry keratin fibers a dye composition comprising, in the presence of at least one oxidizing agent, at least one compound of formula (VI) or (VII) and leaving the composition to act for a time sufficient to develop the desired coloration.

The present disclosure makes it possible to overcome the problems of stability of the direct dye in the dye composition. Indeed, the direct dye is in the form of a precursor, which is more stable than the dye itself.

Moreover, the dyes are synthesized in a simple manner during the application of the dye composition to the fibers, or shortly before this application.

Processes for synthesizing tetraazapentamethine derivatives are known. Some of these processes include using an azine with one molar equivalent of hydrazone, in the presence of an oxidizing agent. One such process is described in FR 1,291,555.

However, in contrast with processes of this type, and entirely unexpectedly, the processes of the disclosure do not require the presence of hydrazone.

Finally, the dyes synthesized according to the processes of the disclosure make it possible to obtain highly chromatic colorations, including the "fundamental" shades, for instance blacks and browns. In addition, they are light-stable and resistant to bad weather and to perspiration.

Other characteristics and advantages of the present disclosure will become evident upon reading the description and the examples that follow.

For the purposes of the present disclosure, organic or mineral anions are chosen, for example, from halides such as chloride, bromide, fluoride and iodide; hydroxides; sulfates; hydrogen sulfates; ($C_1$-$C_6$)alkyl sulfates, for instance methyl sulfate and ethyl sulfate; acetates; tartrate; oxalates; ($C_1$-$C_6$) alkylsulfonates such as methylsulfonate; and arylsulfonates that are unsubstituted or substituted with a $C_1$-$C_4$ alkyl radical, for instance 4-tolylsulfonate.

The compounds of formula (I), whose synthesis constitutes one aspect of the disclosure, will first be described.

In one embodiment of the disclosure, $R_0$ is chosen from hydrogen; linear and branched $C_1$-$C_6$ alkyl radicals that are unsubstituted or substituted with one to three substituents chosen from hydroxyl, $C_1$-$C_2$ alkoxy, $C_2$-$C_4$ (poly)hydroxyalkoxy, amino, $C_1$-$C_2$ (di)alkylamino, $C_2$-$C_4$ (poly)hydroxyalkylamino, carboxyl and sulfonic radicals; phenyl radicals that are unsubstituted or substituted with one to three substituents chosen from hydroxyl, $C_1$-$C_2$ alkoxy, $C_2$-$C_4$ (poly)hydroxyalkoxy, amino, $C_1$-$C_2$ (di)alkylamino, carboxyl and sulfonic radicals, halogen atoms such as chlorine, fluorine and bromine; and optionally-cationic heteroaryl radicals chosen from pyrazolyl, pyrrolyl, imidazolyl, thiazolyl, oxazolyl, triazolyl, pyridyl, pyrimidinyl, triazinyl, pyrazinyl and pyridazinyl radicals.

According to one aspect of this embodiment, $R_0$ is chosen from hydrogen; linear and branched $C_1$-$C_3$ alkyl radicals that are unsubstituted or substituted with one or two substituents chosen from hydroxyl, $C_1$-$C_2$ alkoxy, amino, $C_1$-$C_2$ (di) alkylamino, carboxyl and sulfonic radicals; phenyl radicals that are unsubstituted or substituted with one or two substituents chosen from hydroxyl, amino, $C_1$-$C_2$ (di)alkylamino and $C_2$-$C_4$ (poly)hydroxyalkylamino radicals; and optionally-cationic heteroaryl radicals chosen from pyrazolyl, pyrrolyl, imidazolyl and pyridyl radicals.

According to another aspect of this embodiment, $R_0$ is chosen from hydrogen; methyl, ethyl, propyl, butyl, 2-hydroxyethyl, 2-aminoethyl, 1-carboxymethyl, 2-carboxyethyl, 2-sulfonylethyl, and 2-methoxyethyl radicals; phenyl radicals that are unsubstituted or substituted with one or two substituents chosen from amino, $C_1$-$C_2$ (di)alkylamino and $C_2$-$C_4$ (poly)hydroxyalkylamino radicals; and optionally-cationic heteroaryl radicals chosen from pyrazolyl, pyrrolyl, imidazolyl and pyridyl radicals.

By way of non-limiting example, $R_0$ is chosen from hydrogen; methyl, ethyl and 2-methoxyethyl radicals; phenyl radicals that are unsubstituted or substituted with one substituent chosen from an amino, (di)methylamino and (di)(2-hydroxyethyl)amino radical; and optionally-cationic heteroaryl radicals chosen from imidazolyl and pyridyl radicals.

According to another embodiment of the present disclosure, the radicals $R_2$, $R_6$, $R_{10}$ and $R_{16}$, which may be identical or different, are chosen from hydrogen; phenyl radicals; and $C_1$-$C_4$ alkyl radicals that are unsubstituted or substituted with one or two substituents chosen from hydroxyl, amino, $C_1$-$C_2$ (di)alkylamino and carboxyl radicals.

By way of non-limiting example, the radicals $R_2$, $R_6$, $R_{10}$ and $R_{16}$, which may be identical or different, are chosen from hydrogen; methyl, phenyl, 2-hydroxymethyl and carboxyl radicals; and phenyl radicals.

In accordance with another embodiment, the radicals $R_1$, $R_4$, $R_5$, $R_7$, $R_9$, $R_{15}$, $R_{21}$ and $R_{22}$, which may be identical or different, are chosen from $C_1$-$C_4$ alkyl radicals that are unsubstituted or substituted with one or two substituents chosen from hydroxyl, $C_1$-$C_2$ alkoxy, amino, $C_1$-$C_2$ (di)alkylamino, carboxyl and sulfonic radicals.

According to another aspect of this embodiment, the radicals $R_1$, $R_4$, $R_5$, $R_7$, $R_9$, $R_{15}$, $R_{21}$ and $R_{22}$, which may be identical or different, are chosen from methyl, ethyl, 2-hydroxyethyl, 1-carboxymethyl, 2-carboxyethyl and 2-sulfonylethyl radicals.

According to another embodiment, the $R_3$, $R_8$, $R_{11}$, $R_{12}$, $R_{13}$, $R_{14}$, $R_{17}$, $R_{18}$, $R_{19}$ and $R_{20}$ radicals, which may be identical or different, are chosen from hydrogen atom; linear and branched $C_1$-$C_4$ alkyl radicals that are unsubstituted or substituted with one or two substituents chosen from hydroxyl, $C_1$-$C_2$ alkoxy, $C_2$-$C_4$ (poly)hydroxyalkoxy, amino, $C_1$-$C_2$ (di)alkylamino, carboxyl and sulfonic radicals; phenyl radicals that are unsubstituted or substituted with one or two substituents chosen from hydroxyl, $C_1$-$C_2$ alkoxy, $C_2$-$C_4$ (poly)hydroxyalkoxy, amino, $C_1$-$C_2$ (di)alkylamino, carboxyl and sulfonic radicals, and halogen atoms such as chlorine, fluorine and bromine; sulfonylamino radicals; and $C_2$-$C_4$ (poly)hydroxyalkylamino radicals.

According to another aspect of this embodiment, $R_3$, $R_8$, $R_{11}$, $R_{12}$, $R_{13}$, $R_{14}$, $R_{17}$, $R_{18}$, $R_{19}$ and $R_{20}$, which may be identical or different, are chosen from hydrogen; $C_1$-$C_4$ alkyl radicals that are unsubstituted or substituted with one or two substituents chosen from hydroxyl radicals and $C_1$-$C_2$ alkoxy radicals; amino radicals; $C_1$-$C_2$ (di)alkylamino radicals; carboxyl radicals; and $C_2$-$C_4$ (poly)hydroxyalkylamino radicals.

In accordance with yet another aspect of this embodiment, the radicals $R_3$, $R_8$, $R_{11}$, $R_{12}$, $R_{13}$, $R_{14}$, $R_{17}$, $R_{18}$, $R_{19}$ and $R_{20}$, which may be identical or different, are chosen from hydrogen; methyl, 2-hydroxymethyl, carboxyl, methoxy, ethoxy and 2-hydroxyethyloxy radicals; and amino, methylamino, dimethylamino and 2-hydroxyethylamino radicals.

The compounds of formula (I) that may be made according to the present disclosure include, but are not limited to, those in which $W_1$ is a 2-pyridinium radical and $W_2$ is a 2-pyridine radical.

Compounds in which $W_1$ is a 2-pyridinium radical and $W_2$ is a 2-pyridine radical include, but are not limited to:
2-[5-(N-methyl-2-pyridinylidene)-1-formazano]-N-methylpyridinium chloride,
2-[5-(N-methyl-2-pyridinylidene)-3-methyl-1-formazano]-N-methylpyridinium chloride,
2-[5-(N-methyl-2-pyridinylidene)-3-ethyl-1-formazano]-N-methylpyridinium chloride,
2-[5-(N-methyl-2-pyridinylidene)-3-isopropyl-1-formazano]-N-methylpyridinium chloride,
2-[5-(N-methyl-2-pyridinylidene)-3-phenyl-1-formazano]-N-methylpyridinium chloride,
2-[5-(N-methyl-2-pyridinylidene)-3-(4'-methoxyphenyl)-1-formazano]-N-methylpyridinium,
2-[5-(N-methyl-2-pyridinylidene)-3-(4'-hydroxyphenyl)-1-formazano]-N-methylpyridinium chloride,
2-[5-(N-methyl-2-pyridinylidene)-3-(4'-N,N-dimethylaminophenyl)-1-formazano]-N-methylpyridinium chloride,
2-[5-(4-pyrrolidino-N-methyl-2-pyridinylidene)-1-formazano]-4-pyrrolidino-N-methylpyridinium chloride,
2-[5-(4-pyrrolidino-N-methyl-2-pyridinylidene)-3-methyl-1-formazano]-4-pyrrolidino-N-methylpyridinium chloride,
2-[5-(4-pyrrolidino-N-methyl-2-pyridinylidene)-3-ethyl-1-formazano]-4-pyrrolidino-N-methylpyridinium chloride,
2-[5-(4-pyrrolidino-N-methyl-2-pyridinylidene)-3-isopropyl-1-formazano]-4-pyrrolidino-N-methylpyridinium chloride,
2-[5-(4-pyrrolidino-N-methyl-2-pyridinylidene)-3-phenyl-1-formazano]-4-pyrrolidino-N-methylpyridinium chloride,
2-[5-(4-pyrrolidino-N-methyl-2-pyridinylidene)-3-(4'-methoxyphenyl)-1-formazano]-4-pyrrolidino-N-methylpyridinium chloride,
2-[5-(4-pyrrolidino-N-methyl-2-pyridinylidene)-3-(4'-hydroxyphenyl)-1-formazano]-4-pyrrolidino-N-methylpyridinium chloride,
2-[5-(4-pyrrolidino-N-methyl-2-pyridinylidene)-3-(4'-N,N-dimethylaminophenyl)-1-formazano]-4-pyrrolidino-N-methylpyridinium chloride,
2-[5-(N-hydroxyethyl-2-pyridinylidene)-1-formazano]-N-hydroxyethylpyridinium chloride,
2-[5-(N-hydroxyethyl-2-pyridinylidene)-3-methyl-1-formazano]-N-hydroxyethylpyridinium chloride,
2-[5-(N-hydroxyethyl-2-pyridinylidene)-3-ethyl-1-formazano]-N-hydroxyethylpyridinium chloride,
2-[5-(N-hydroxyethyl-2-pyridinylidene)-3-phenyl-1-formazano]-N-hydroxyethylpyridinium chloride,
2-[5-(N-hydroxyethyl-2-pyridinylidene)-3-isopropyl-1-formazano]-N-hydroxyethylpyridinium chloride,
2-[5-(N-hydroxyethyl-2-pyridinylidene)-3-(4'-methoxyphenyl)-1-formazano]-N-hydroxyethylpyridinium chloride,
2-[5-(N-hydroxyethyl-2-pyridinylidene)-3-(4'-hydroxyphenyl)-1-formazano]-N-hydroxyethylpyridinium chloride,
2-[5-(N-hydroxyethyl-2-pyridinylidene)-3-(4'-N,N-dimethylaminophenyl)-1-formazano]-N-hydroxyethylpyridinium chloride,
2-[5-(N-carboxyethyl-2-pyridinylidene)-1-formazano]-N-carboxyethylpyridinium chloride,
2-[5-(N-carboxyethyl-2-pyridinylidene)-3-methyl-1-formazano]-N-carboxyethylpyridinium chloride,
2-[5-(N-carboxyethyl-2-pyridinylidene)-3-ethyl-1-formazano]-N-carboxyethylpyridinium chloride,
2-[5-(N-carboxyethyl-2-pyridinylidene)-3-phenyl-1-formazano]-N-carboxyethylpyridinium chloride,
2-[5-(N-carboxyethyl-2-pyridinylidene)-3-isopropyl-1-formazano]-N-carboxyethylpyridinium chloride,
2-[5-(N-carboxyethyl-2-pyridinylidene)-3-(4'-methoxyphenyl)-1-formazano]-N-carboxyethylpyridinium chloride,
2-[5-(N-carboxyethyl-2-pyridinylidene)-3-(4'-hydroxyphenyl)-1-formazano]-N-carboxyethylpyridinium chloride, and
2-[5-(N-carboxyethyl-2-pyridinylidene)-3-(4'-N,N-dimethylaminophenyl)-1-formazano]-N-carboxyethylpyridinium chloride.

The compounds of formula (I) that may be made according to the disclosure also include, but are not limited to, those in which $W_1$ is a 4-pyridinium radical and $W_2$ is a 4-pyridine radical.

Compounds in which $W_1$ is a 4-pyridinium radical and $W_2$ is a 4-pyridine radical include, but are not limited to:
4-[5-(N-methyl-4-pyridinylidene)-1-formazano]-N-methylpyridinium chloride,
4-[5-(N-methyl-4-pyridinylidene)-3-methyl-1-formazano]-N-methylpyridinium chloride,
4-[5-(N-methyl-4-pyridinylidene)-3-ethyl-1-formazano]-N-methylpyridinium chloride,
4-[5-(N-methyl-4-pyridinylidene)-3-isopropyl-1-formazano]-N-methylpyridinium chloride,
4-[5-(N-methyl-4-pyridinylidene)-3-phenyl-1-formazano]-N-methylpyridinium chloride,
4-[5-(N-methyl-4-pyridinylidene)-3-(4'-methoxyphenyl)-1-formazano]-N-methylpyridinium chloride,
4-[5-(N-methyl-4-pyridinylidene)-3-(4'-hydroxyphenyl)-1-formazano]-N-methylpyridinium chloride,
4-[5-(N-methyl-4-pyridinylidene)-3-(4'-N,N-dimethylaminophenyl)-1-formazano]-N-methylpyridinium chloride,
4-[5-(N-hydroxyethyl-4-pyridinylidene)-1-formazano]-N-hydroxyethylpyridinium chloride,
4-[5-(N-hydroxyethyl-4-pyridinylidene)-3-methyl-1-formazano]-N-hydroxyethylpyridinium chloride,
4-[5-(N-hydroxyethyl-4-pyridinylidene)-3-ethyl-1-formazano]-N-hydroxyethylpyridinium chloride,
4-[5-(N-hydroxyethyl-4-pyridinylidene)-3-phenyl-1-formazano]-N-hydroxyethylpyridinium chloride,
4-[5-(N-hydroxyethyl-4-pyridinylidene)-3-isopropyl-1-formazano]-N-hydroxyethylpyridinium chloride,
4-[5-(N-hydroxyethyl-4-pyridinylidene)-3-(4'-methoxyphenyl)-1-formazano]-N-hydroxyethylpyridinium chloride,
4-[5-(N-hydroxyethyl-4-pyridinylidene)-3-(4'-hydroxyphenyl)-1-formazano]-N-hydroxyethylpyridinium chloride,
4-[5-(N-hydroxyethyl-4-pyridinylidene)-3-(4'-N,N-dimethylaminophenyl)-1-formazano]-N-hydroxyethylpyridinium chloride,
4-[5-(N-carboxyethyl-4-pyridinylidene)-1-formazano]-N-carboxyethylpyridinium chloride,
4-[5-(N-carboxyethyl-4-pyridinylidene)-3-methyl-1-formazano]-N-carboxyethylpyridinium chloride,
4-[5-(N-carboxyethyl-4-pyridinylidene)-3-ethyl-1-formazano]-N-carboxyethylpyridinium chloride,
4-[5-(N-carboxyethyl-4-pyridinylidene)-3-phenyl-1-formazano]-N-carboxyethylpyridinium chloride,
4-[5-(N-carboxyethyl-4-pyridinylidene)-3-isopropyl-1-formazano]-N-carboxyethylpyridinium chloride,
4-[5-(N-carboxyethyl-4-pyridinylidene)-3-(4'-methoxyphenyl)-1-formazano]-N-carboxyethylpyridinium chloride,
4-[5-(N-carboxyethyl-4-pyridinylidene)-3-(4'-hydroxyphenyl)-1-formazano]-N-carboxyethylpyridinium chloride, and 4-[5-(N-carboxyethyl-4-pyridinylidene)-3-(4'-N,N-dimethylaminophenyl)-1-formazano]-N-carboxyethylpyridinium chloride.

The compounds of formula (I) that may be made according to the disclosure also include, but are not limited to, those in which $W_1$ is a 2-imidazolium radical and $W_2$ is a 2-imidazole radical.

Compounds in which $W_1$ is a 2-imidazolium radical and $W_2$ is a 2-imidazole radical include, but are not limited to:
2-[5-(1,3-dimethyl-2-imidazolidene)-1-formazano]-1,3-dimethylimidazolium chloride,
2-[5-(1,3-dimethyl-2-imidazolidene)-3-methyl-1-formazano]-1,3-dimethylimidazolium chloride,
2-[5-(1,3-dimethyl-2-imidazolidene)-3-ethyl-1-formazano]-1,3-dimethylimidazolium chloride,
2-[5-(1,3-dimethyl-2-imidazolidene)-3-isopropyl-1-formazano]-1,3-dimethylimidazolium chloride,
2-[5-(1,3-dimethyl-2-imidazolidene)-3-phenyl-1-formazano]-1,3-dimethylimidazolium chloride,
2-[5-(1,3-dimethyl-2-imidazolidene)-3-(4'-methoxyphenyl)-1-formazano]-1,3-dimethylimidazolium chloride,
2-[5-(1,3-dimethyl-2-imidazolidene)-3-(4'-hydroxyphenyl)-1-formazano]-1,3-dimethylimidazolium chloride,
2-[5-(1,3-dimethyl-2-imidazolidene)-3-(4'-N,N-dimethylaminophenyl)-1-formazano]-1,3-dimethylimidazolium chloride,
2-[5-(1,3-dihydroxyethyl-2-imidazolidene)-1-formazano]-1,3-dihydroxyethylimidazolium chloride,
2-[5-(1,3-dihydroxyethyl-2-imidazolidene)-3-methyl-1-formazano]-1,3-dihydroxyethylimidazolium chloride,
2-[5-(1,3-dihydroxyethyl-2-imidazolidene)-3-ethyl-1-formazano]-1,3-dihydroxyethylimidazolium chloride,
2-[5-(1,3-dihydroxyethyl-2-imidazolidene)-3-phenyl-1-formazano]-1,3-dihydroxyethylimidazolium chloride,
2-[5-(1,3-dihydroxyethyl-2-imidazolidene)-3-isopropyl-1-formazano]-1,3-dihydroxyethylimidazolium chloride,
2-[5-(1,3-dihydroxyethyl-2-imidazolidene)-3-(4'-methoxyphenyl)-1-formazano]-1,3-dihydroxyethylimidazolium chloride,
2-[5-(1,3-dihydroxyethyl-2-imidazolidene)-3-(4'-hydroxyphenyl)-1-formazano]-1,3-dihydroxyethylimidazolium chloride,
2-[5-(1,3-dihydroxyethyl-2-imidazolidene)-3-(4'-N,N-dimethylaminophenyl)-1-formazano]-1,3-dihydroxyethylimidazolium chloride,
2-[5-(1,3-dicarboxyethyl-2-imidazolidene)-1-formazano]-1,3-dicarboxyethylimidazolium chloride,
2-[5-(1,3-dicarboxyethyl-2-imidazolidene)-3-methyl-1-formazano]-1,3-dicarboxyethylimidazolium chloride,
2-[5-(1,3-dicarboxyethyl-2-imidazolidene)-3-ethyl-1-formazano]-1,3-dicarboxyethylimidazolium chloride,
2-[5-(1,3-dicarboxyethyl-2-imidazolidene)-3-phenyl-1-formazano]-1,3-dicarboxyethylimidazolium chloride,
2-[5-(1,3-dicarboxyethyl-2-imidazolidene)-3-isopropyl-1-formazano]-1,3-dicarboxyethylimidazolium chloride,
2-[5-(1,3-dicarboxyethyl-2-imidazolidene)-3-(4'-methoxyphenyl)-1-formazano]-1,3-dicarboxyethylimidazolium chloride,
2-[5-(1,3-dicarboxyethyl-2-imidazolidene)-3-(4'-hydroxyphenyl)-1-formazano]-1,3-dicarboxyethylimidazolium chloride, and
2-[5-(1,3-dicarboxyethyl-2-imidazolidene)-3-(4'-N,N-dimethylaminophenyl)-1-formazano]-1,3-dicarboxyethylimidazolium chloride.

The compounds of formula (I) that may be made according to the present disclosure also include, but are not limited to, those in which $W_1$ is a 5-pyrazolium radical and $W_2$ is a 5-pyrazole radical.

Compounds in which $W_1$ is a 5-pyrazolium radical and $W_2$ is a 5-pyrazole radical include, but are not limited to:
5-[5-(1,2-dimethyl-5-pyrazolidene)-1-formazano]-1,2-dimethylpyrazolinium chloride,
5-[5-(1,2-dimethyl-5-pyrazolidene)-3-methyl-1-formazano]-1,2-dimethylpyrazolinium chloride,
5-[5-(1,2-dimethyl-5-pyrazolidene)-3-ethyl-1-formazano]-1,2-dimethylpyrazolinium chloride,
5-[5-(1,2-dimethyl-5-pyrazolidene)-3-isopropyl-1-formazano]-1,2-dimethylpyrazolinium chloride,
5-[5-(1,2-dimethyl-5-pyrazolidene)-3-phenyl-1-formazano]-1,2-dimethylpyrazolinium chloride,
5-[5-(1,2-dimethyl-5-pyrazolidene)-3-(4'-methoxyphenyl)-1-formazano]-1,2-dimethylpyrazolinium chloride,
5-[5-(1,2-dimethyl-5-pyrazolidene)-3-(4'-hydroxyphenyl)-1-formazano]-1,2-dimethylpyrazolinium chloride,
5-[5-(1,2-dimethyl-5-pyrazolidene)-3-(4'-N,N-dimethylaminophenyl)-1-formazano]-1,2-dimethylpyrazolinium chloride,
5-[5-(1,2-dihydroxyethyl-5-pyrazolidene)-1-formazano]-1,2-dihydroxyethylpyrazolinium chloride,
5-[5-(1,2-dihydroxyethyl-5-pyrazolidene)-3-methyl-1-formazano]-1,2-dihydroxyethylpyrazolinium chloride,
5-[5-(1,2-dihydroxyethyl-5-pyrazolidene)-3-ethyl-1-formazano]-1,2-dihydroxyethylpyrazolinium chloride,
5-[5-(1,2-dihydroxyethyl-5-pyrazolidene)-3-phenyl-1-formazano]-1,2-dihydroxyethylpyrazolinium chloride,
5-[5-(1,2-dihydroxyethyl-5-pyrazolidene)-3-isopropyl-1-formazano]-1,2-dihydroxyethylpyrazolinium chloride,
5-[5-(1,2-dihydroxyethyl-5-pyrazolidene)-3-(4'-methoxyphenyl)-1-formazano]-1,2-dihydroxyethylpyrazolinium chloride,
5-[5-(1,2-dihydroxyethyl-5-pyrazolidene)-3-(4'-hydroxyphenyl)-1-formazano]-1,2-dihydroxyethylpyrazolinium chloride,
5-[5-(1,2-dihydroxyethyl-5-pyrazolidene)-3-(4'-N,N-dimethylaminophenyl)-1-formazano]-1,2-dihydroxyethylpyrazolinium chloride,
5-[5-(1,2-dicarboxyethyl-5-pyrazolidene)-1-formazano]-1,2-dicarboxyethylpyrazolinium chloride,
5-[5-(1,2-dicarboxyethyl-5-pyrazolidene)-3-methyl-1-formazano]-1,2-dicarboxyethylpyrazolinium chloride,
5-[5-(1,2-dicarboxyethyl-5-pyrazolidene)-3-ethyl-1-formazano]-1,2-dicarboxyethylpyrazolinium chloride,
5-[5-(1,2-dicarboxyethyl-5-pyrazolidene)-3-phenyl-1-formazano]-1,2-dicarboxyethylpyrazolinium chloride,
5-[5-(1,2-dicarboxyethyl-5-pyrazolidene)-3-isopropyl-1-formazano]-1,2-dicarboxyethylpyrazolinium chloride,
5-[5-(1,2-dicarboxyethyl-5-pyrazolidene)-3-(4'-methoxyphenyl)-1-formazano]-1,2-dicarboxyethylpyrazolinium chloride,
5-[5-(1,2-dicarboxyethyl-5-pyrazolidene)-3-(4'-hydroxyphenyl)-1-formazano]-1,2-dicarboxyethylpyrazolinium chloride, and
5-[5-(1,2-dicarboxyethyl-5-pyrazolidene)-3-(4'-N,N-dimethylaminophenyl)-1-formazano]-1,2-dicarboxyethylpyrazolinium chloride.

The compounds of formula (I) that may be made according to the present disclosure also include, but are not limited to, those in which $W_1$ is a 2-benzimidazolium radical and $W_2$ is a 2-pyridine radical.

Compounds in which $W_1$ is a 2-benzimidazolium radical and $W_2$ is a 2-pyridine radical include, but are not limited to:

2-[5-(N-methyl-2-pyridinylidene)-1-formazano]-1,3-dimethylbenzimidazolium chloride,
2-[5-(N-methyl-2-pyridinylidene)-3-methyl-1-formazano]-1,3-dimethylbenzimidazolium chloride,
2-[5-(N-methyl-2-pyridinylidene)-3-ethyl-1-formazano]-1,3-dimethylbenzimidazolium chloride,
2-[5-(N-methyl-2-pyridinylidene)-3-isopropyl-1-formazano]-1,3-dimethylbenzimidazolium chloride,
2-[5-(N-methyl-2-pyridinylidene)-3-phenyl-1-formazano]-1,3-dimethylbenzimidazolium chloride,
2-[5-(N-methyl-2-pyridinylidene)-3-(4'-methoxyphenyl)-1-formazano]-1,3-dimethylbenzimidazolium chloride,
2-[5-(N-methyl-2-pyridinylidene)-3-(4'-hydroxyphenyl)-1-formazano]-1,3-dimethylbenzimidazolium chloride,
2-[5-(N-methyl-2-pyridinylidene)-3-(4'-N,N-dimethylaminophenyl)-1-formazano]-1,3-dimethylbenzimidazolium chloride,
2-[5-(N-hydroxyethyl-2-pyridinylidene)-1-formazano]-1,3-dihydroxyethylbenzimidazolium chloride,
2-[5-(N-hydroxyethyl-2-pyridinylidene)-3-methyl-1-formazano]-1,3-dihydroxyethylbenzimidazolium chloride,
2-[5-(N-hydroxyethyl-2-pyridinylidene)-3-ethyl-1-formazano]-1,3-dihydroxyethylbenzimidazolium chloride,
2-[5-(N-hydroxyethyl-2-pyridinylidene)-3-phenyl-1-formazano]-1,3-dihydroxyethylbenzimidazolium chloride,
2-[5-(N-hydroxyethyl-2-pyridinylidene)-3-isopropyl-1-formazano]-1,3-dihydroxyethylbenzimidazolium chloride,
2-[5-(N-hydroxyethyl-2-pyridinylidene)-3-(4'-methoxyphenyl)-1-formazano]-1,3-dihydroxyethylbenzimidazolium chloride,
2-[5-(N-hydroxyethyl-2-pyridinylidene)-3-(4'-hydroxyphenyl)-1-formazano]-1,3-dihydroxyethylbenzimidazolium chloride,
2-[5-(N-hydroxyethyl-2-pyridinylidene)-3-(4'-N,N-dimethylaminophenyl)-1-formazano]-1,3-dihydroxyethylbenzimidazolium chloride,
2-[5-(N-carboxyethyl-2-pyridinylidene)-1-formazano]-1,3-dicarboxyethylbenzimidazolium chloride,
2-[5-(N-carboxyethyl-2-pyridinylidene)-3-methyl-1-formazano]-1,3-dicarboxyethylbenzimidazolium chloride,
2-[5-(N-carboxyethyl-2-pyridinylidene)-3-ethyl-1-formazano]-1,3-dicarboxyethylbenzimidazolium chloride,
2-[5-(N-carboxyethyl-2-pyridinylidene)-3-phenyl-1-formazano]-1,3-dicarboxyethylbenzimidazolium chloride,
2-[5-(N-carboxyethyl-2-pyridinylidene)-3-isopropyl-1-formazano]-1,3-dicarboxyethylbenzimidazolium chloride,
2-[5-(N-carboxyethyl-2-pyridinylidene)-3,4'-methoxyphenyl)-1-formazano]-1,3-dicarboxyethylbenzimidazolium chloride,
2-[5-(N-carboxyethyl-2-pyridinylidene)-3-(4'-hydroxyphenyl)-1-formazano]-1,3-dicarboxyethylbenzimidazolium chloride, and
2-[5-(N-carboxyethyl-2-pyridinylidene)-3-(4'-N,N-dimethylaminophenyl)-1-formazano]-1,3-dicarboxyethylbenzimidazolium chloride.

Compounds of formula (I) that may be made according to the present disclosure also include, but are not limited to, those in which $W_1$ is a 2-benzimidazolium radical and $W_2$ is a 4-pyridine radical.

Compounds in which $W_1$ is a 2-benzimidazolium radical and $W_2$ is a 4-pyridine radical include, but are not limited to:
2-[5-(N-methyl-4-pyridinylidene)-1-formazano]-1,3-dimethylbenzimidazolium chloride,
2-[5-(N-methyl-4-pyridinylidene)-3-methyl-1-formazano]-1,3-dimethylbenzimidazolium chloride,
2-[5-(N-methyl-4-pyridinylidene)-3-ethyl-1-formazano]-1,3-dimethylbenzimidazolium chloride,
2-[5-(N-methyl-4-pyridinylidene)-3-isopropyl-1-formazano]-1,3-dimethylbenzimidazolium chloride,
2-[5-(N-methyl-4-pyridinylidene)-3-phenyl-1-formazano]-1,3-dimethylbenzimidazolium chloride,
2-[5-(N-methyl-4-pyridinylidene)-3-(4'-methoxyphenyl)-1-formazano]-1,3-dimethylbenzimidazolium chloride,
2-[5-(N-methyl-4-pyridinylidene)-3-(4'-hydroxyphenyl)-1-formazano]-1,3-dimethylbenzimidazolium chloride,
2-[5-(N-methyl-4-pyridinylidene)-3-(4'-N,N-dimethylaminophenyl)-1-formazano]-1,3-dimethylbenzimidazolium chloride,
2-[5-(N-hydroxyethyl-4-pyridinylidene)-1-formazano]-1,3-dihydroxyethylbenzimidazolium chloride,
2-[5-(N-hydroxyethyl-4-pyridinylidene)-3-methyl-1-formazano]-1,3-dihydroxyethylbenzimidazolium chloride,
2-[5-(N-hydroxyethyl-4-pyridinylidene)-3-ethyl-1-formazano]-1,3-dihydroxyethylbenzimidazolium chloride,
2-[5-(N-hydroxyethyl-4-pyridinylidene)-3-phenyl-1-formazano]-1,3-dihydroxyethylbenzimidazolium chloride,
2-[5-(N-hydroxyethyl-4-pyridinylidene)-3-isopropyl-1-formazano]-1,3-dihydroxyethylbenzimidazolium chloride,
2-[5-(N-hydroxyethyl-4-pyridinylidene)-3-(4'-methoxyphenyl)-1-formazano]-1,3-dihydroxyethylbenzimidazolium chloride,
2-[5-(N-hydroxyethyl-4-pyridinylidene)-3-(4'-hydroxyphenyl)-1-formazano]-1,3-dihydroxyethylbenzimidazolium chloride,
2-[5-(N-hydroxyethyl-4-pyridinylidene)-3-(4'-N,N-dimethylaminophenyl)-1-formazano]-1,3-dihydroxyethylbenzimidazolium chloride,
2-[5-(N-carboxyethyl-4-pyridinylidene)-1-formazano]-1,3-dicarboxyethylbenzimidazolium chloride,
2-[5-(N-carboxyethyl-4-pyridinylidene)-3-methyl-1-formazano]-1,3-dicarboxyethylbenzimidazolium chloride,
2-[5-(N-carboxyethyl-4-pyridinylidene)-3-ethyl-1-formazano]-1,3-dicarboxyethylbenzimidazolium chloride,
2-[5-(N-carboxyethyl-4-pyridinylidene)-3-phenyl-1-formazano]-1,3-dicarboxyethylbenzimidazolium chloride,
2-[5-(N-carboxyethyl-4-pyridinylidene)-3-isopropyl-1-formazano]-1,3-dicarboxyethylbenzimidazolium chloride,
2-[5-(N-carboxyethyl-4-pyridinylidene)-3,4'-methoxyphenyl)-1-formazano]-1,3-dicarboxyethylbenzimidazolium chloride,
2-[5-(N-carboxyethyl-4-pyridinylidene)-3-(4'-hydroxyphenyl)-1-formazano]-1,3-dicarboxyethylbenzimidazolium chloride, and
2-[5-(N-carboxyethyl-4-pyridinylidene)-3-(4'-N,N-dimethylaminophenyl)-1-formazano]-1,3-dicarboxyethylbenzimidazolium chloride.

Compounds of formula (I) that may be made according to the present disclosure also include, but are not limited to, those in which $W_1$ is a 2-imidazolium radical and $W_2$ is a-2-pyridine radical.

Compounds in which $W_1$ is a 2-imidazolium radical and $W_2$ is a 2-pyridine radical include, but are not limited to:
2-[5-(N-methyl-2-pyridinylidene)-1-formazano]-1,3-dimethylimidazolium chloride,
2-[5-(N-methyl-2-pyridinylidene)-3-methyl-1-formazano]-1,3-dimethylimidazolium chloride,
2-[5-(N-methyl-2-pyridinylidene)-3-ethyl-1-formazano]-1,3-dimethylimidazolium chloride,
2-[5-(N-methyl-2-pyridinylidene)-3-isopropyl-1-formazano]-1,3-dimethylimidazolium chloride,
2-[5-(N-methyl-2-pyridinylidene)-3-phenyl-1-formazano]-1,3-dimethylimidazolium chloride,
2-[5-(N-methyl-2-pyridinylidene)-3-(4'-methoxyphenyl)-1-formazano]-1,3-dimethylimidazolium chloride, 2-[5-(N-methyl-2-pyridinylidene)-3-(4'-hydroxyphenyl)-1-formazano]-1,3-dimethylimidazolium chloride,
2-[5-(N-methyl-2-pyridinylidene)-3-(4'-N,N-dimethylaminophenyl)-1-formazano]-1,3-dimethylimidazolium chloride,
2-[5-(N-hydroxyethyl-2-pyridinylidene)-1-formazano]-1,3-dihydroxyethylimidazolium chloride,
2-[5-(N-hydroxyethyl-2-pyridinylidene)-3-methyl-1-formazano]-1,3-dihydroxyethylimidazolium chloride,
2-[5-(N -hydroxyethyl-2-pyridinylidene)-3-ethyl-1-formazano]-1,3-dihydroxyethylimidazolium chloride,
2-[5-(N-hydroxyethyl-2-pyridinylidene)-3-phenyl-1-formazano]-1,3-dihydroxyethylimidazolium chloride,
2-[5-(N-hydroxyethyl-2-pyridinylidene)-3-isopropyl-1-formazano]-1,3-dihydroxyethylimidazolium chloride,
2-[5-(N-hydroxyethyl-2-pyridinylidene)-3-(4'-methoxyphenyl)-1-formazano]-1,3-dihydroxyethylimidazolium chloride,
2-[5-(N-hydroxyethyl-2-pyridinylidene)-3-(4'-hydroxyphenyl)-1-formazano]-1,3-dihydroxyethylimidazolium chloride,
2-[5-(N-hydroxyethyl-2-pyridinylidene)-3-(4'-N,N-dimethylaminophenyl)-1-formazano]-1,3-dihydroxyethylimidazolium chloride,
2-[5-(N-carboxyethyl-2-pyridinylidene)-1-formazano]-1,3-dicarboxyethylimidazolium chloride,
2-[5-(N-carboxyethyl-2-pyridinylidene)-3-methyl-1-formazano]-1,3-dicarboxyethylimidazolium chloride,
2-[5-(N-carboxyethyl-2-pyridinylidene)-3-ethyl-1-formazano]-1,3-dicarboxyethylimidazolium chloride,
2-[5-(N-carboxyethyl-2-pyridinylidene)-3-phenyl-1-formazano]-1,3-dicarboxyethylimidazolium chloride,
2-[5-(N-carboxyethyl-2-pyridinylidene)-3-isopropyl-1-formazano]-1,3-dicarboxyethylimidazolium chloride,
2-[5-(N-carboxyethyl-2-pyridinylidene)-3-(4'-methoxyphenyl)-1-formazano]-1,3-dicarboxyethylimidazolium chloride,
2-[5-(N-carboxyethyl-2-pyridinylidene)-3-(4'-hydroxyphenyl)-1-formazano]-1,3-dicarboxyethylimidazolium chloride, and
2-[5-(N-carboxyethyl-2-pyridinylidene)-3-(4'-N,N-dimethylaminophenyl)-1-formazano]-1,3-dicarboxyethylimidazolium chloride.

Compounds of formula (I) that may be made according to the present disclosure also include, but are not limited to, those in which $W_1$ is a 2-imidazolium radical and $W_2$ is a 4-pyridine radical.

Compounds in which $W_1$ is a 2-imidazolium radical and $W_2$ is a 4-pyridine radical include, but are not limited to:
2-[5-(N-methyl-4-pyridinylidene)-1-formazano]-1,3-dimethylimidazolium chloride,
2-[5-(N-methyl-4-pyridinylidene)-3-methyl-1-formazano]-1,3-dimethylimidazolium chloride,
2-[5-(N-methyl-4-pyridinylidene)-3-ethyl-1-formazano]-1,3-dimethylimidazolium chloride,
2-[5-(N-methyl-4-pyridinylidene)-3-isopropyl-1-formazano]-1,3-dimethylimidazolium chloride,
2-[5-(N-methyl-4-pyridinylidene)-3-phenyl-1-formazano]-1,3-dimethylimidazolium chloride,
2-[5-(N-methyl-4-pyridinylidene)-3-(4'-methoxyphenyl)-1-formazano]-1,3-dimethylimidazolium chloride,
2-[5-(N-methyl-4-pyridinylidene)-3-(4'-hydroxyphenyl)-1-formazano]-1,3-dimethylimidazolium chloride,
2-[5-(N-methyl-4-pyridinylidene)-3-(4'-N,N-dimethylaminophenyl)-1-formazano]-1,3-dimethylimidazolium chloride,
2-[5-(N-hydroxyethyl-4-pyridinylidene)-1-formazano]-1,3-dihydroxyethylimidazolium chloride,
2-[5-(N-hydroxyethyl-4-pyridinylidene)-3-methyl-1-formazano]-1,3-dihydroxyethylimidazolium chloride,
2-[5-(N-hydroxyethyl-4-pyridinylidene)-3-ethyl-1-formazano]-1,3-dihydroxyethylimidazolium chloride,
2-[5-(N-hydroxyethyl-4-pyridinylidene)-3-phenyl-1-formazano]-1,3-dihydroxyethylimidazolium chloride,
2-[5-(N-hydroxyethyl-4-pyridinylidene)-3-isopropyl-1-formazano]-1,3-dihydroxyethylimidazolium chloride,
2-[5-(N-hydroxyethyl-4-pyridinylidene)-3-(4'-methoxyphenyl)-1-formazano]-1,3-dihydroxyethylimidazolium chloride,
2-[5-(N-hydroxyethyl-4-pyridinylidene)-3-(4'-hydroxyphenyl)-1-formazano]-1,3-dihydroxyethylimidazolium chloride,
2-[5-(N-hydroxyethyl-4-pyridinylidene)-3-(4'-N,N-dimethylaminophenyl)-1-formazano]-1,3-dihydroxyethylimidazolium chloride,
2-[5-(N-carboxyethyl-4-pyridinylidene)-1-formazano]-1,3-dicarboxyethylimidazolium chloride,
2-[5-(N-carboxyethyl-4-pyridinylidene)-3-methyl-1-formazano]-1,3-dicarboxyethylimidazolium chloride,
2-[5-(N-carboxyethyl-4-pyridinylidene)-3-ethyl-1-formazano]-1,3-dicarboxyethylimidazolium chloride,
2-[5-(N-carboxyethyl-4-pyridinylidene)-3-phenyl-1-formazano]-1,3-dicarboxyethylimidazolium chloride,
2-[5-(N-carboxyethyl-4-pyridinylidene)-3-isopropyl-1-formazano]-1,3-dicarboxyethylimidazolium chloride,
2-[5-(N-carboxyethyl-4-pyridinylidene)-3-(4'-methoxyphenyl)-1-formazano]-1,3-dicarboxyethylimidazolium chloride,
2-[5-(N-carboxyethyl-4-pyridinylidene)-3-(4'-hydroxyphenyl)-1-formazano]-1,3-dicarboxyethylimidazolium chloride, and
2-[5-(N-carboxyethyl-4-pyridinylidene)-3-(4'-N,N-dimethylaminophenyl)-1-formazano]-1,3-dicarboxyethylimidazolium chloride.

Compounds of formula (I) that may be made according to the present disclosure also include, but are not limited to, those in which $W_1$ is a 2-benzimidazolium radical and $W_2$ is a 2-benzimidazole radical.

Compounds in which $W_1$ is a 2-benzimidazolium radical and $W_2$ is a 2-benzimidazole radical include, but are not limited to:
2-[5-(1,3-dimethyl-2-benzimidazolidene)-1-formazano]-1,3-dimethylbenzimidazolium chloride,
2-[5-(1,3-dimethyl-2-benzimidazolidene)-3-methyl-1-formazano]-1,3-dimethylbenzimidazolium chloride,
2-[5-(1,3-dimethyl-2-benzimidazolidene)-3-ethyl-1-formazano]-1,3-dimethylbenzimidazolium chloride,
2-[5-(1,3-dimethyl-2-benzimidazolidene)-3-isopropyl-1-formazano]-1,3-dimethylbenzimidazolium chloride,
2-[5-(1,3-dimethyl-2-benzimidazolidene)-3-phenyl-1-formazano]-1,3-dimethylbenzimidazolium chloride,
2-[5-(1,3-dimethyl-2-benzimidazolidene)-3-(4'-methoxyphenyl)-1-formazano]-1,3-dimethylbenzimidazolium chloride,
2-[5-(1,3-dimethyl-2-benzimidazolidene)-3-(4'-hydroxyphenyl)-1-formazano]-1,3-dimethylbenzimidazolium chloride,
2-[5-(1,3-dimethyl-2-benzimidazolidene)-3-(4'-N,N-dimethylaminophenyl)-1-formazano]-1,3-dimethylbenzimidazolium chloride,
2-[5-(1,3-dihydroxyethyl-2-benzimidazolidene)-1-formazano]-1,3-dihydroxyethylbenzimidazolium chloride, 2-[5-(1,3-dihydroxyethyl-2-benzimidazolidene)-3-methyl-1-formazano]-1,3-dihydroxyethylbenzimi chloride, 2-[5-(1,3-dihydroxyethyl-2-benzimidazolidene)-3-ethyl-1-formazano]-1,3-dihydroxyethylbenzimidazolium chloride, 2-[5-(1,3-dihydroxyethyl-2-benzimidazolidene)-3-phenyl-1-formazano]-1,3-dihydroxyethylbenzimidazolium chloride, 2-[5-(1,3-dihydroxyethyl-2-benzimidazolidene)-3-isopropyl-1-formazano]-1,3-dihydroxyethylbenzimidazolium chloride, 2-[5-(1,3-dihydroxyethyl-2-benzimidazolidene)-3-(4'-methoxyphenyl)-1-formazano]-1,3-dihydroxyethylbenzimidazolium chloride, 2-[5-(1,3-dihydroxyethyl-2-benzimidazolidene)-3-(4'-hydroxyphenyl)-1-formazano]-1,3-dihydroxyethylbenzimidazolium chloride, 2-[5-(1,3-dihydroxyethyl-2-benzimidazolidene)-3-(4'-N,N-dimethylaminophenyl)-1-formazano]-1,3-dihydroxyethylbenzimidazolium chloride, 2-[5-(1,3-dicarboxyethyl-2-benzimidazolidene)-1-formazano]-1,3-dicarboxyethylbenzimidazolium chloride, 2-[5-(1,3-dicarboxyethyl-2-benzimidazolidene)-3-methyl-1-formazano]-1,3-dicarboxyethylbenzimidazolium chloride, 2-[5-(1,3-dicarboxyethyl-2-benzimidazolidene)-3-ethyl-1-formazano]-1,3-dicarboxyethylbenzimidazolium chloride, 2-[5-(1,3-dicarboxyethyl-2-benzimidazolidene)-3-phenyl-1-formazano]-1,3-dicarboxyethylbenzimidazolium chloride, 2-[5-(1,3-dicarboxyethyl-2-benzimidazolidene)-3-isopropyl-1-formazano]-1,3-dicarboxyethylbenzimidazolium chloride, 2-[5-(1,3-dicarboxyethyl-2-benzimidazolidene)-3-(4'-methoxyphenyl)-1-formazano]-1,3-dicarboxyethylbenzimidazolium chloride, 2-[5-(1,3-dicarboxyethyl-2-benzimidazolidene)-3-(4'-hydroxyphenyl)-1-formazano]-1,3-dicarboxyethylbenzimidazolium chloride, and 2-[5-(1,3-dicarboxyethyl-2-benzimidazolidene)-3-(4'-N,N-dimethylaminophenyl)-1-formazano]-1,3-dicarboxyethylbenzimidazolium chloride.

As mentioned previously, processes for synthesizing the compounds that have just been described comprise reacting, in the presence of at least one oxidizing agent, at least one azine compound of formula (VI) and/or (VII):

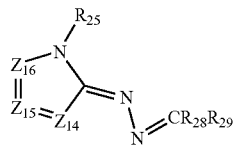

formula (VI)

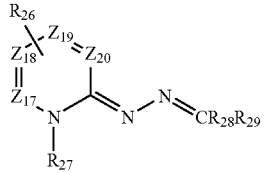

formula (VII)

wherein:

$Z_{14}$ is chosen from oxygen, sulfur, $NR_9$ radicals, and $NR_{15}$ radicals, $Z_{15}$ is chosen from nitrogen, $CR_{10}$ radicals, and $CR_{16}$ radicals, $Z_{16}$ is chosen from $CR_2$ radicals, $CR_6$ radicals, nitrogen, $NR_{21}$ radicals, and $NR_{22}$ radicals, $R_{25}$ is a linear or branched $C_1$-$C_8$ alkyl radical that is unsubstituted or substituted with one to three substituents chosen from hydroxyl, $C_1$-$C_2$ alkoxy, $C_2$-$C_4$ (poly)hydroxyalkoxy, amino, $C_1$-$C_2$ (di)alkylamino, carboxyl and sulfonic radicals, $Z_{17}$ is chosen from nitrogen, $CR_{11}$ radicals, and $CR_{17}$ radicals, $Z_{18}$ is chosen from nitrogen, $CR_{12}$ radicals, and $CR_{18}$ radicals, $Z_{19}$ is chosen from nitrogen, $CR_{13}$ radicals, and $CR_{19}$ radicals, $Z_{20}$ is chosen from nitrogen, $CR_{14}$ radicals, and $CR_{20}$ radicals, $R_{26}$ is chosen from hydrogen; linear and branched $C_1$-$C_{16}$ hydrocarbon-based chains, wherein the chains are optionally saturated or unsaturated with one to three unsaturations, wherein the chains are unsubstituted or substituted with one to three substituents chosen from hydroxyl, $C_1$-$C_2$ alkoxy, $C_2$-$C_4$ (poly)hydroxyalkoxy, amino, $C_1$-$C_2$ (di)alkylamino, carboxyl, sulfonic, sulfonylamino and $C_2$-$C_4$ (poly)hydroxyalkylamino radicals, and halogen atoms such as chlorine, fluorine and bromine, and wherein the chains may be interrupted by one or two oxygen, nitrogen, or sulfur atoms, or by an $SO_2$ radical; phenyl radicals that are unsubstituted or substituted with one to three substituents chosen from hydroxyl, $C_1$-$C_2$ alkoxy, $C_2$-$C_4$ (poly)hydroxyalkoxy, amino, $C_1$-$C_2$ (di)alkylamino, carboxyl, sulfonic, sulfonylamino and $C_2$-$C_4$ (poly)hydroxyalkylamino radicals, and halogen atoms such as chlorine, fluorine and bromine; and heteroaryl radicals chosen from pyrazolyl, pyrrolyl, imidazolyl, thiazolyl, oxazolyl, triazolyl, pyridyl, pyrimidinyl, triazinyl, pyrazinyl and pyridazinyl radicals, $R_{27}$ is a linear or branched $C_1$-$C_8$ alkyl radical that is unsubstituted or substituted with one to three substituents chosen from hydroxyl, $C_1$-$C_2$ alkoxy, $C_2$-$C_4$ (poly)hydroxyalkoxy, amino, $C_1$-$C_2$ (di)alkylamino, carboxyl and sulfonic radicals, $R_{28}$ and $R_{29}$, which may be identical or different, are chosen from hydrogen; $C_1$-$C_6$ alkyl radicals, such as $C_1$-$C_4$ alkyl radicals; and linear and branched $C_1$-$C_6$ alkoxy radicals, such as $C_1$-$C_4$ alkoxy radicals, wherein at least one of the two radicals $R_{28}$ and $R_{29}$ is not hydrogen.

Everything that has been stated previously regarding the nature of the radicals $Z_1$ to $Z_{16}$ and $R_1$, $R_3$, $R_4$, $R_5$, $R_7$, and $R_8$ remains valid in this section of the description, and reference may be made thereto.

According to one embodiment of the present disclosure, $R_{28}$ and $R_{29}$, which may be identical or different, are chosen from hydrogen, methyl radicals and methoxy radicals.

According to another embodiment of the disclosure, the oxidizing agent can be chosen from hydrogen peroxide; urea peroxide; organic peracids such as peracetic acid; persalts such as permanganate and perborate; persulfates; chromates and dichromates; hypochlorites; hypobromites; ferricyanides; and manganese dioxide and lead dioxide, alone or as mixtures.

For example, the oxidizing agent can be hydrogen peroxide.

According to another embodiment of the present disclosure, the oxidizing agents can be chosen from enzymes in the presence of suitable substrates.

Within the context of this embodiment, enzymes that may be used as oxidizing agents include, but are not limited to, oxidases that produce hydrogen peroxide when they are in the presence of a suitable substrate.

Non-limiting examples of enzymes of this type include:

| | |
|---|---|
| PYRANOSE OXIDASE | EC 1.1.3.10 |
| L-SORBOSE OXIDASE | EC 1.1.3.11 |
| PYRIDOXINE 4-OXIDASE | EC 1.1.3.12 |
| ALCOHOL OXIDASE | EC 1.1.3.13 |
| CATECHOL OXIDASE (DIMERIZING) | EC 1.1.3.14 |
| (S)-2-HYDROXY-ACID OXIDASE | EC 1.1.3.15 |
| ECDYSONE OXIDASE | EC 1.1.3.16 |
| CHOLINE OXIDASE | EC 1.1.3.17 |
| SEC-ALCOHOL OXIDASE | EC 1.1.3.18 |
| 4-HYDROXYMANDALATE OXIDASE | EC 1.1.3.19 |
| LONG-CHAIN-ALCOHOL OXIDASE | EC 1.1.3.20 |
| GLYCEROL-3-PHOSPHATE OXIDASE | EC 1.1.3.21 |
| XANTHINE OXIDASE | EC 1.1.3.22 |
| THIAMIN OXIDASE | EC 1.1.3.23 |
| L-GALACTONOLACTONE OXIDASE | EC 1.1.3.24 |
| CELLOBIOSE OXIDASE | EC 1.1.3.25 |
| HYDROXYPHYTANATE OXIDASE | EC 1.1.3.27 |
| NUCLEOSIDE OXIDASE | EC 1.1.3.28 |
| N-ACYLHEXOSAMINE OXIDASE | EC 1.1.3.29 |
| MALATE OXIDASE | EC 1.1.3.3 |
| POLYVINYL-ALCOHOL OXIDASE | EC 1.1.3.30 |
| METHANOL OXIDASE | EC 1.1.3.31 |
| D-ARABINONO-1,4-LACTONE OXIDASE | EC 1.1.3.37 |
| VANILLYL-ALCOHOL OXIDASE | EC 1.1.3.38 |
| NUCLEOSIDE OXIDASE (H(2)O(2)-FORMING) | EC 1.1.3.39 |
| GLUCOSE OXIDASE | EC 1.1.3.4 |
| D-MANNITOL OXIDASE | EC 1.1.3.40 |
| XYLITOL OXIDASE | EC 1.1.3.41 |
| HEXOSE OXIDASE | EC 1.1.3.5 |
| CHOLESTEROL OXIDASE | EC 1.1.3.6 |
| ARYL ALCOHOL OXIDASE | EC 1.1.3.7 |
| L-GULONOLACTONE OXIDASE | EC 1.1.3.8 |
| GALACTOSE OXIDASE | EC 1.1.3.9 |
| PTERIDINE OXIDASE | EC 1.17.3.1 |
| RETINAL OXIDASE | EC 1.2.3.11 |
| ALDEHYDE OXIDASE | EC 1.2.3.1 |
| CARBON MONOXIDE OXIDASE | EC 1.2.3.10 |
| VANILLATE DEMETHYLASE | EC 1.2.3.12 |
| 4-HYDROXYPHENYLPYRUVATE OXIDASE | EC 1.2.3.13 |
| PYRUVATE OXIDASE | EC 1.2.3.3 |
| OXALATE OXIDASE | EC 1.2.3.4 |
| GLYOXALATE OXIDASE | EC 1.2.3.5 |
| PYRUVATE OXIDASE (CO-A ACETYLATING) | EC 1.2.3.6 |
| INDOLE-3-ACETALDEHYDE OXIDASE | EC 1.2.3.7 |
| PYRIDOXAL OXIDASE | EC 1.2.3.8 |
| ARYL ALDEHYDE OXIDASE | EC 1.2.3.9 |
| DUHYDROOROTATE OXIDASE | EC 1.3.3.1 |
| LATHOSTEROL OXIDASE | EC 1.3.3.2 |
| COPROPORPHYRINOGEN OXIDASE | EC 1.3.3.3 |
| PROTOPORPHYRINOGEN OXIDASE | EC 1.3.3.4 |
| BILIRUBIN OXIDASE | EC 1.3.3.5 |
| ACYL CO-A OXIDASE | EC 1.3.3.6 |
| DIHYDROURACIL OXIDASE | EC 1.3.3.7 |
| TETRAHYDROBERBERINE OXIDASE | EC 1.3.3.8 |
| SECOLOGANIN SYNTHASE | EC 1.3.3.9 |
| ASPARTATE OXIDASE | EC 1.4.3.1 |
| PUTRESCINE OXIDASE | EC 1.4.3.10 |
| L-GLUTAMATE OXIDASE | EC 1.4.3.11 |
| CYCLOHEXYLAMINE OXIDASE | EC 1.4.3.12 |
| PROTEIN-LYSINE 6-OXIDASE | EC 1.4.3.13 |
| L-LYSINE OXIDASE | EC 1.4.3.14 |
| D-GLUTAMATE (D-ASPARTATE) OXIDASE | EC 1.4.3.15 |
| L-ASPARTATE OXIDASE | EC 1.4.3.16 |
| TRYPTOPHAN ALPHA, BETA-OXIDASE | EC 1.4.3.17 |
| GLYCINE OXIDASE | EC 1.4.3.19 |
| L-AMINO ACID OXIDASE | EC 1.4.3.2 |

-continued

| | |
|---|---|
| D-AMINO ACID OXIDASE | EC 1.4.3.3 |
| AMINE OXIDASE (FLAVIN CONTAINING) | EC 1.4.3.4 |
| PYRIDOXAMINE PHOSPHATE OXIDASE | EC 1.4.3.5 |
| AMINE OXIDASE (COPPER CONTAINING) | EC 1.4.3.6 |
| D-GLUTAMATE OXIDASE | EC 1.4.3.7 |
| ETHANOLAMINE OXIDASE | EC 1.4.3.8 |
| SARCOSINE OXIDASE | EC 1.5.3.1 |
| DIMETHYLGLYCINE OXIDASE | EC 1.5.3.10 |
| POLYAMINE OXIDASE | EC 1.5.3.11 |
| DIHYDROBENZOPHENANTHRIDINE OXIDASE | EC 1.5.3.12 |
| N-METHYL-L-L-AMINO ACID OXIDASE | EC 1.5.3.2 |
| N-METHYL-LYSINE OXIDASE | EC 1.5.3.4 |
| (S)-6-HYDROXYNICOTINE OXIDASE | EC 1.5.3.5 |
| (R)-6-HYDROXYNICOTINE OXIDASE | EC 1.5.3.6 |
| L-PIPECOLATE OXIDASE | EC 1.5.3.7 |
| RETICULATE OXIDASE | EC 1.5.3.9 |
| NITROETHANE OXIDASE | EC 1.7.3.1 |
| ACETYLINDOXYL OXIDASE | EC 1.7.3.2 |
| URATE OXIDASE | EC 1.7.3.3 |
| HYDROXYLAMINE OXIDASE | EC 1.7.3.4 |
| 3-ACYL-NITROPROPANOATE OXIDASE | EC 1.7.3.5 |
| SULFITE OXIDASE | EC 1.8.3.1 |
| THIOL OXIDASE | EC 1.8.3.2 |
| GLUTATHIONE OXIDASE | EC 1.8.3.3 |
| METHANETHIOL OXIDASE | EC 1.8.3.4 |
| PRENYLCYSTEINE OXIDASE | EC 1.8.3.5 |

Still in the context of this embodiment, enzymes that may be used as oxidizing agents also include, but are not limited to, 4-electron oxidoreductase enzymes.

Non-limiting examples of this type of enzyme include enzymes from the group EC 1.10.3, for instance catechol oxidase, also known as polyphenol oxidase (EC 1.10.3.1), laccase (EC 1.10.3.2), L-ascorbate oxidase (EC 1.10.3.3), aminophenol oxidase (EC 1.10.3.4), and tyrosinase, also known as monophenol oxidase (EC 1.10.3.1 or 1.14.18.1).

Still in the context of this embodiment, enzymes that may be used as oxidizing agents also include, but are not limited to, peroxidases.

Non-limiting examples of enzymes of this type include:

| | |
|---|---|
| NADH peroxidase | E.C 1.11.1.1 |
| NADPH peroxidase | E.C 1.11.1.2 |
| Fatty acid peroxidase | E.C 1.11.1.3 |
| Cytochrome-c peroxidase | E.C 1.11.1.5 |
| Peroxidase | E.C 1.11.1.7 |
| Iodide peroxidase | E.C 1.11.1.8 |
| Glutathione peroxidase | E.C 1.11.1.9 |
| Chloride peroxidase | E.C 1.11.1.10 |
| L-ascorbate peroxidase | E.C 1.11.1.11 |
| Phospholipid-hydroperoxide glutathione peroxidase | E.C 1.11.1.12 |
| Manganese peroxidase | E.C 1.11.1.13 |
| Diarylpropane peroxidase | E.C 1.11.1.14 |
| Tryptophan 2,3-dioxygenase | E.C 1.13.11.11 |
| Lipoxygenase | E.C 1.13.11.12 |

Depending on the reagents used, the reaction is performed with or without an oxidizing system, with or without a co-factor for the enzyme, and with or without a co-factor regeneration system.

It should be noted that the term "without an oxidizing system" means that no oxidizing system other than atmospheric oxygen is used for the reaction.

For example, the reaction can be performed in aerobic medium at a pH ranging from 3 to 11, and at a temperature ranging from 6° C. to 80° C.

The concentration of enzyme substrate, whether or not this substrate is other than azine, can range from 0.001M to 3M, such as from 0.1M to 1M.

The co-factor for the enzymes can be present in an amount ranging from 0.01 mM to 10 mM, such as from 0.1 mM to 1 mM.

The reaction may be performed at a pH ranging from 3 to 11, such as from 5 to 9.5.

Usually, the reaction is performed in aqueous medium and/or in the presence of a protic solvent, for example alcohols, polyols and polyol ethers.

The pH of the medium can be adjusted, or if necessary kept constant, by means of acidifying and basifying agents, and by using a standard buffer.

The reaction temperature may range from 10° C. to 80° C., such as from 20° C. to 65° C.

According to one embodiment of the disclosure, in setting up the synthesis of the compounds of formula (I), the reagents, that is, the azine(s) of formulae (VI) and/or (VII); the enzymatic system, including the enzyme(s), the substrate thereof, the co-factor thereof, the oxidizing agent and/or, where appropriate, the co-factor regeneration system; and the oxidizing agent, are mixed together and the pH and the temperature are adjusted.

The processes of the disclosure may be performed continuously.

A second subject of the present disclosure relates to processes for dyeing keratin fibers, for example human keratin fibers, comprising:

applying to wet or dry fibers, in the presence of an oxidizing agent, a dye composition comprising at least one azine of formula (VI) and/or (VII):

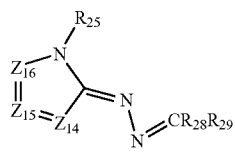

formula (VI)

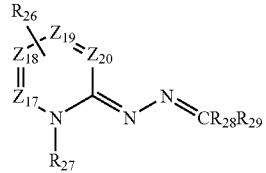

formula (VII)

wherein:

$Z_{14}$ is chosen from oxygen, sulfur, $NR_9$ radicals, and $NR_{15}$ radicals, $Z_{15}$ is chosen from nitrogen, $CR_{10}$ radicals, and $CR_{16}$ radicals, $Z_{16}$ is chosen from $CR_2$ radicals, $CR_6$ radicals, nitrogen, $NR_{21}$ radicals, and $NR_{22}$ radicals, $R_{25}$ is a linear or branched $C_1$-$C_8$ alkyl radical that is unsubstituted or substituted with one to three substituents chosen from hydroxyl, $C_1$-$C_2$ alkoxy, $C_2$-$C_4$ (poly)hydroxyalkoxy, amino, $C_1$-$C_2$ (di)alkylamino, carboxyl and sulfonic radicals, $Z_{17}$ is chosen from nitrogen, $CR_{11}$ radicals, and $CR_{17}$ radicals, $Z_{18}$ is chosen from nitrogen, $CR_{12}$ radicals, and $CR_{18}$ radicals, $Z_{19}$ is chosen from nitrogen, $CR_{13}$ radicals, and $CR_{19}$ radicals, $Z_{20}$ is chosen from nitrogen, $CR_{14}$ radicals, and $CR_{20}$ radicals, $R_{26}$ is chosen from hydrogen; linear and branched $C_1$-$C_{16}$ hydrocarbon-based chains, wherein the chains are optionally saturated or unsaturated with one to three unsaturations, wherein the chains are unsubstituted or substituted with one to three substituents chosen from hydroxyl, $C_1$-$C_2$ alkoxy, $C_2$-$C_4$ (poly)hydroxyalkoxy, amino, $C_1$-$C_2$ (di)alkylamino, carboxyl, sulfonic, sulfonylamino and $C_2$-$C_4$ (poly)hydroxyalkylamino radicals, and halogen atoms such as chlorine, fluorine and bromine, and wherein the chains may be interrupted by one or two oxygen, nitrogen, or sulfur atoms, or by an $SO_2$ radical; phenyl radicals that are unsubstituted or substituted with one to three substituents chosen from hydroxyl, $C_1$-$C_2$ alkoxy, $C_2$-$C_4$ (poly)hydroxyalkoxy, amino, $C_1$-$C_2$ (di)alkylamino, carboxyl, sulfonic, sulfonylamino and $C_2$-$C_4$ (poly)hydroxyalkylamino radicals, and halogen atoms such as chlorine, fluorine and bromine; and heteroaryl radicals chosen from pyrazolyl, pyrrolyl, imidazolyl, thiazolyl, oxazolyl, triazolyl, pyridyl, pyrimidinyl, triazinyl, pyrazinyl and pyridazinyl radicals, $R_{27}$ is a linear or branched $C_1$-$C_8$ alkyl radical that is unsubstituted or substituted with one to three substituents chosen from hydroxyl, $C_1$-$C_2$ alkoxy, $C_2$-$C_4$ (poly)hydroxyalkoxy, amino, $C_1$-$C_2$ (di)alkylamino, carboxyl and sulfonic radicals, $R_{28}$ and $R_{29}$, which may be identical or different, are chosen from hydrogen; $C_1$-$C_6$ alkyl radicals, such as $C_1$-$C_4$ alkyl radicals; and linear and branched $C_1$-$C_6$ alkoxy radicals, such as $C_1$-$C_4$ alkoxy radicals, and must be chosen such that at least one of the two radicals is not hydrogen.

leaving the composition to act for a period of time sufficient to develop the desired coloration.

The oxidizing agent may be mixed with the dye composition at the time of use.

It may also be applied to the fibers simultaneously with or sequentially to the dye composition.

Compound(s) of formula (VI) and/or (VII) can be present in an amount such that the composition comprises compound(s) of formula (I) in an amount ranging from of 0.001% to 10% by weight, relative to the total weight of the composition, such as from 0.05% to 5% by weight, relative to the total weight of the dye composition.

For example, compound(s) of formula (VI) and/or (VII) can be present in the dye composition in an amount ranging from 0.001% to 10% by weight, relative to the total weight of the composition, such as from 0.05% to 5% by weight, relative to the total weight of the dye composition.

The dye composition used in the processes according to the disclosure may further comprise at least one additional direct dye.

The at least one additional direct dye may be chosen from compounds that are different from the compound(s) of formula (I) synthesized during the reaction, such as from compounds belonging to a different chemical family, or from compounds belonging to the same chemical family but having at least one different substituent.

Any type of direct dye conventionally used in the field of hair dyeing may be used. Non-limiting examples that may be mentioned include neutral, acidic and cationic nitrobenzene direct dyes; neutral, acidic and cationic azo direct dyes; neutral, acidic and cationic quinone and in particular anthraquinone direct dyes; azine direct dyes; methine direct dyes; triarylmethane direct dyes; indoamine dyes; and natural direct dyes.

If the composition does comprise at least one additional direct dye, the dye can be present in an amount ranging from 0.001% to 20% by weight, relative to the total weight of the dye composition, such as from 0.005% to 10% by weight, relative to the total weight of the dye composition.

The composition may also further comprise at least one oxidation base optionally combined with at least one coupler.

This at least one oxidation base may be chosen from the oxidation bases conventionally used in oxidation dyeing, for example, but not limited to, para-phenylenediamines, bis (phenyl)alkylenediamines, para-aminophenols, ortho-aminophenols and heterocyclic bases.

When the dye composition comprises at least one oxidation base, the oxidation base(s) can be present in an amount ranging from 0.001% to 10% by weight, relative to the total weight of the dye composition, such as from 0.005% to 6% by weight, relative to the total weight of the dye composition.

Among the couplers that may be used, non-limiting examples include meta-phenylenediamines, meta-aminophenols, meta-diphenols, naphthalene-based couplers and heterocyclic couplers.

When the dye composition comprises at least one coupler, the coupler(s) can be present in an amount ranging from 0.001% to 10% by weight, relative to the total weight of the dye composition, such as from 0.005% to 6% by weight, relative to the total weight of the dye composition.

In general, the direct dyes, the oxidation bases and the couplers may be used in the form of an addition salt, for example with an acid. These acids are usually chosen from the hydrochlorides, hydrobromides, sulfates, citrates, succinates, tartrates, lactates, tosylates, benzenesulfonates, phosphates and acetates.

The medium of the dye composition, also known as the dye support, generally consists of water or comprises water and at least one organic solvent to dissolve the compounds that would not be sufficiently water-soluble.

Among the organic solvents that may be used, non-limiting examples include $C_1$-$C_4$ alcohols such as ethanol and isopropanol; polyols and polyol ethers, for instance 2-butoxyethanol, propylene glycol, propylene glycol monomethyl ether, diethylene glycol monoethyl ether and monomethyl ether; aromatic alcohols, for instance benzyl alcohol and phenoxyethanol; and mixtures thereof.

The organic solvents can be present in an amount ranging from 1% to 40% by weight, relative to the total weight of the dye composition, such as from 5% to 30% by weight, relative to the total weight of the dye composition.

The dye composition in accordance with the disclosure may further comprise various adjuvants conventionally used in compositions for dyeing the hair, such as anionic, cationic, nonionic, amphoteric and zwitterionic surfactants and mixtures thereof; anionic, cationic, nonionic, amphoteric and zwitterionic polymers and mixtures thereof; mineral and organic thickeners, for example anionic, cationic, nonionic and amphoteric associative polymers; antioxidants; penetrating agents; sequestering agents; fragrances; buffers; dispersants; conditioning agents, for instance volatile and nonvolatile, modified and unmodified silicones; film-forming agents; ceramides; preserving agents; and opacifiers.

Each adjuvant mentioned can be present in an amount ranging from 0.01% to 20% by weight, relative to the total weight of the composition.

A person skilled in the art will take care to select this or these optional additional compound(s) such that the advantageous properties intrinsically associated with the dye composition in accordance with the disclosure are not, or are not substantially, adversely affected by the envisaged addition(s).

The pH of the dye composition applied during processes in accordance with the disclosure can range from 3 to 12, such as from 5 to 11. The pH may be adjusted to the desired value by means of acidifying and basifying agents usually used in the dyeing of keratin fibers, and of standard buffer systems.

Among the acidifying agents that may be used, non-limiting examples include mineral and organic acids, for instance hydrochloric acid, orthophosphoric acid, and sulfuric acid; carboxylic acids, for instance acetic acid, tartaric acid, citric acid and lactic acid; and sulfonic acids.

Among the basifying agents that may be used, non-limiting examples include aqueous ammonia; alkali metal carbonates; alkanolamines such as mono-ethanolamine, diethanolamine and triethanolamine and derivatives thereof; sodium hydroxide; potassium hydroxide; and the compounds of formula (VIII):

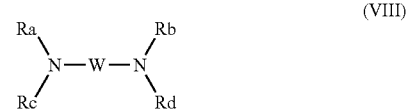

wherein:
W is a propylene residue optionally substituted with a substituent chosen from hydroxyl groups and $C_1$-$C_4$ alkyl radicals,
$R_a$, $R_b$, $R_c$ and $R_d$, which may be identical or different, are chosen from hydrogen, and $C_1$-$C_4$ alkyl and $C_1$-$C_4$ hydroxyalkyl radicals.

Among the standard volatile and non-volatile buffer systems that may be used, non-limiting examples include triethylammonium acetate, triethylammonium formate and phosphate buffers.

Furthermore, the dye composition may be in various forms, such as in the form of liquids, creams and gels, and in any other form that is suitable for dyeing keratin fibers, for example human keratin fibers such as hair.

The oxidizing composition, whether or not it is mixed with the dye composition before application, may further comprise various adjuvants conventionally used in compositions for dyeing the hair and as defined above.

The pH of the oxidizing composition comprising the oxidizing agent is such that, after mixing with the dye composition, the pH of the resulting composition applied to the keratin fibers can range from 3 to 12, such as from 5 to 11. It may be adjusted to the desired value using acidifying and basifying agents, and buffers usually used in the dyeing of keratin fibers, and as defined above.

The period of time required to develop the desired coloration in step b) depends on several criteria including, inter alia, the application temperature and the temperature at which the dye composition is active.

However, by way of example, the time required to develop the desired coloration can range from 3 to 50 minutes, such as from 5 to 30 minutes.

The temperature at which the composition is applied and then left to act can range from room temperature to 80° C.

The composition that is finally applied to the keratin fibers may be in various forms, such as in the form of liquids, creams and gels, and in any other form that is suitable for dyeing keratin fibers, for example human hair.

The reaction is stopped when the desired colour is obtained. The time required to develop the desired coloration can range from 1 to 60 minutes, such as from 5 to 45 minutes.

Once step b) is complete, the fibers may optionally be rinsed, for example washed with a shampoo and rinsed, and then dried or left to dry.

The disclosure may be understood more clearly with the aid of the non-limiting examples that follow, which constitute preferred embodiments of the compositions according to the invention. Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained herein. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope are approximations, the numerical values set forth in the specific example are reported as precisely as possible. Any numerical value, however, inherently contains certain errors necessarily resulting from the standard deviation found in its respective testing measurements.

EXAMPLES

Example 1

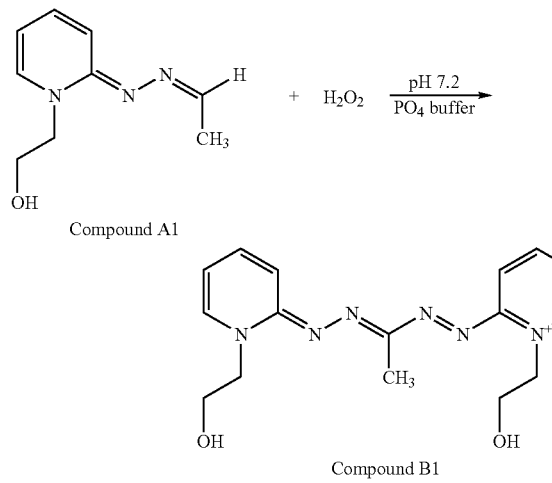

Compound A1

0.58 g of azine (compound A1) was dissolved in 12.5 ml of phosphate buffer (0.2M; pH 7) and the pH was adjusted to 7.2 with 1M sodium hydroxide solution. 10.3 ml of hydrogen peroxide (5 volume strength) were added. The reaction was allowed to take place at room temperature, and the synthesis was stopped after 24 hours.

Analysis of the reaction medium by mass spectrometry in positive electrospray ionization (ESI+) mode made it possible to detect the pseudomolecular ion M+=329. This ion corresponded to compound B1.

Compound B1 was analyzed by LC/UV. It was detected by its UV/visible spectrum at its absorption maximum $\lambda_{max}$=578 nm. In addition, analysis of compound B1 by $^1$H proton NMR, performed in deuterated methanol (CD$_3$OD), gave results in accordance with the expected product.

Example 2

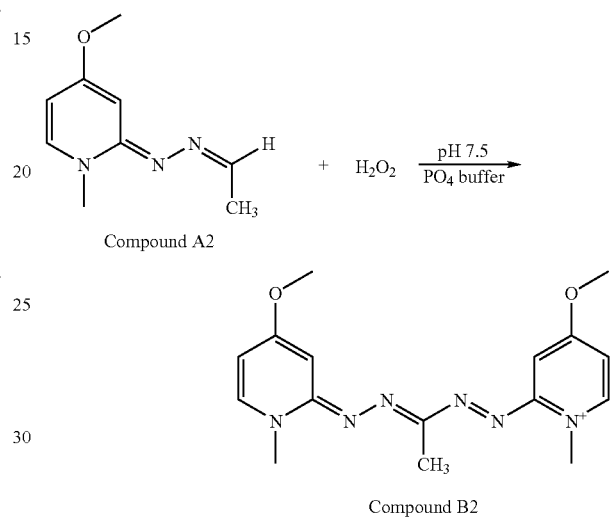

Compound B2

0.1 g of azine (compound A2) was dissolved in 5 ml of a phosphate buffer (0.2M; pH 7) and the pH was adjusted to 7.5 with 1M sodium hydroxide solution. 0.56 ml of hydrogen peroxide (20 volume strength) was added. The reaction was allowed to take place at room temperature, and the synthesis was stopped after one hour.

Analysis of the reaction medium by mass spectrometry in positive electrospray ionization (ESI+) mode made it possible to detect the pseudomolecular ion M+=329. The ion corresponded to compound B2.

Compound B2 was analyzed by LC/UV. It was detected by its UV/visible spectrum at its absorption maximum $\lambda_{max}$=564 nm. In addition, analysis of compound B2 by $^1$H proton NMR, performed in deuterated methanol (CD$_3$OD), was in accordance with the expected product.

Example 3

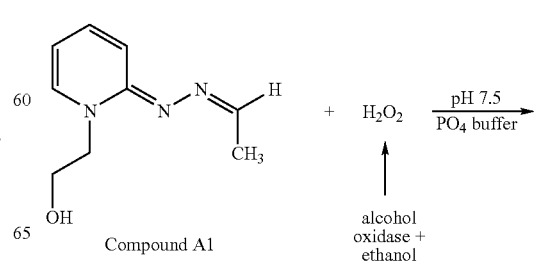

Compound A1

-continued

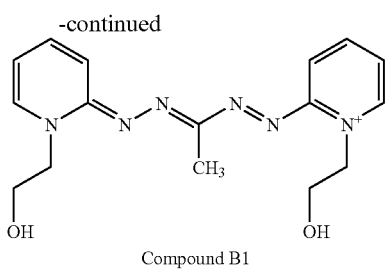

Compound B1

25 mg of azine (compound A1) were dissolved in 5 ml of phosphate buffer (0.2M; pH 7) and the pH was adjusted to 7.5 with 1M sodium hydroxide. 125 µl of absolute ethanol were then added, followed by addition of 60 U of alcohol oxidase enzyme. The solution was then aerated by sparging with air. The reaction was allowed to take place at room temperature, and the synthesis was stopped after one hour.

Analysis of the reaction medium by mass spectrometry in positive electrospray ionization (ESI+) mode made it possible to detect the pseudomolecular ion M+=329. The ion corresponded to compound B1.

Compound B1 was analyzed by LC/UV. It was detected by its UV/visible spectrum at its absorption maximum $\lambda_{max}$=578 nm.

Example 4

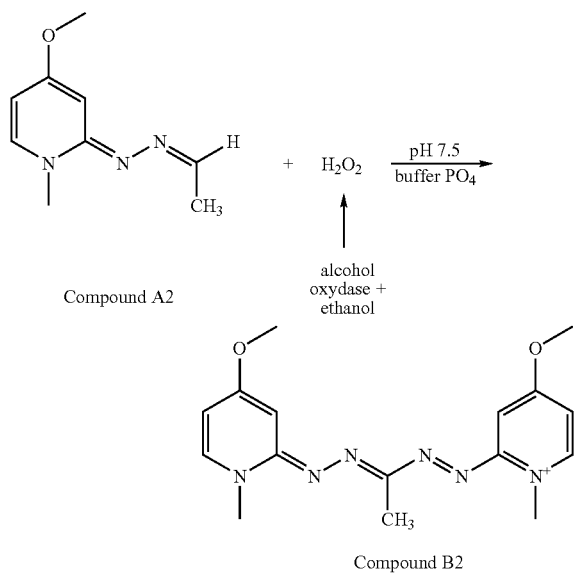

Compound A2

Compound B2

50 mg of the azine (Compound A2) were dissolved in 2.5 ml of phosphate buffer (0.2M; pH 7) and the pH was adjusted to 7.5 with 1M sodium hydroxide. 250 µl of absolute ethanol were then added, followed by addition of 120 U of alcohol oxidase enzyme. The solution was then aerated by sparging with air. The reaction was allowed to take place at room temperature and the synthesis was stopped after one hour.

Analysis of the reaction medium by mass spectrometry in positive electrospray ionization (ESI+) mode made it possible to detect the pseudomolecular ion M+=329. The ion corresponded to compound B2.

Compound B2 was analysed by LC/UV. It was detected via its UV/visible spectrum at its absorption maximum $\lambda_{max}$=564 nm.

Example 5

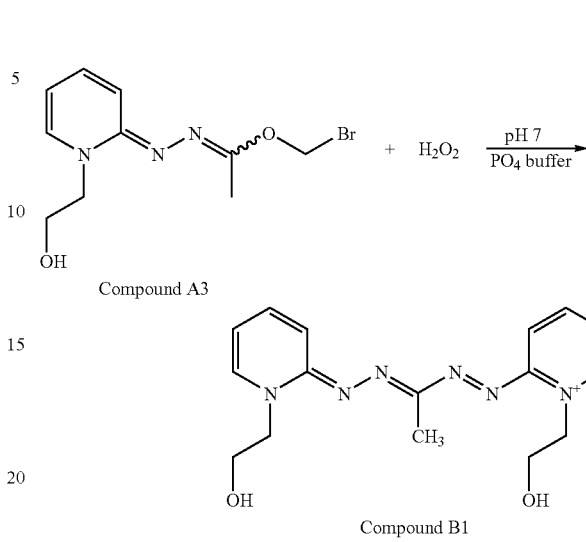

Compound A3

Compound B1

10 mg of azine (compound A3) were dissolved in 2 ml of phosphate buffer (0.2M; pH 7). 100 µl of 20 volume strength hydrogen peroxide were then added. The reaction was allowed to take place at room temperature. After reacting for 1 hour, the solution was blue.

Analysis of the reaction medium by mass spectrometry in positive electrospray ionization (ESI+) mode made it possible to detect the pseudomolecular ion M+=329. The ion corresponded to compound B1.

Compound B1 was analyzed by LC/UV. It was detected via its UV/visible spectrum at its absorption maximum $\lambda_{max}$=578 nm.

Example 6

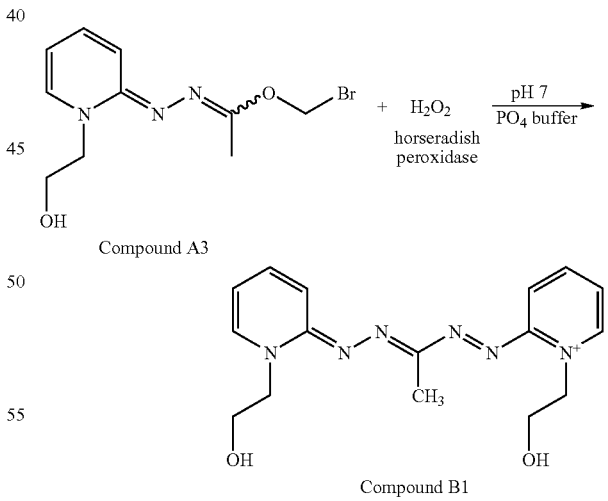

Compound A3

Compound B1

10 mg of azine (compound A3) were dissolved in 2 ml of phosphate buffer (0.2M; pH 7). 100 µl of 20 volume strength hydrogen peroxide were then added, followed by addition of 30 U of horseradish peroxidase. The reaction was allowed to take place at room temperature. After reacting for 15 minutes, the solution was blue.

Analysis of the reaction medium by mass spectrometry in positive electrospray ionization (ESI+) mode made it possible to detect the pseudomolecular ion M+=329. The ion corresponded to compound B1.

Compound B1 was analyzed by LC/UV. It was detected via its UV/visible spectrum at its absorption maximum $\lambda_{max}$=578 nm.

Example 7

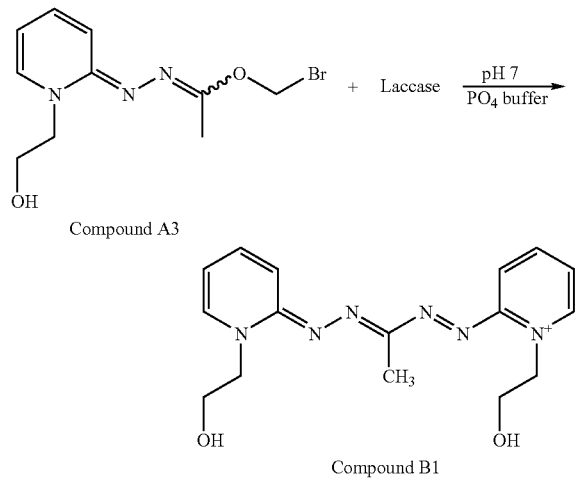

Compound A3

Compound B1

10 g of azine (compound A3) were dissolved in 2 ml of phosphate buffer (0.2M; pH 7). 50 U of laccase were then added. The reaction was allowed to take place at room temperature. After reacting for 30 minutes, the solution was blue.

Analysis of the reaction medium by mass spectrometry in positive electrospray ionization (ESI+) mode made it possible to detect the pseudomolecular ion M+=329. The ion corresponded to compound B1.

Compound B1 was analyzed by LC/UV. It was detected via its UV/visible spectrum at its absorption maximum $\lambda_{max}$=578 nm.

Example 8

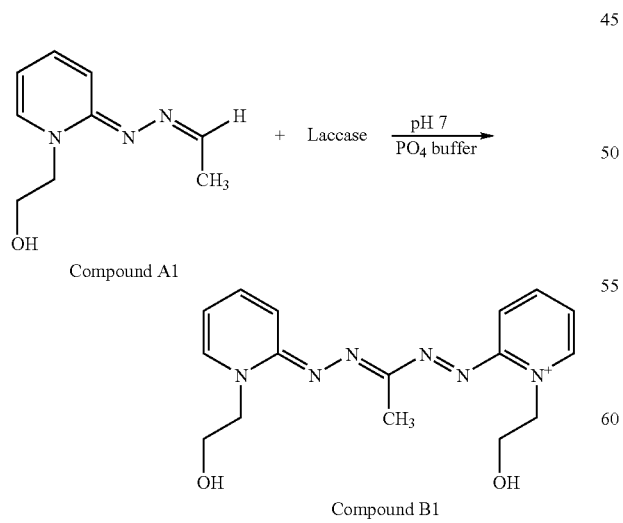

Compound A1

Compound B1

10 mg of azine (compound A1) were dissolved in 2 ml of phosphate buffer (0.2M; pH 7). 50 U of laccase were added. The reaction was allowed to take place at room temperature. After reacting for 30 minutes, the solution was blue.

Analysis of the solution medium by mass spectrometry in positive electrospray ionization (ESI+) mode made it possible to detect the pseudomolecular ion M+=329. The ion corresponded to compound B1.

Compound B1 was analyzed by LC/UV. It was detected via its UV/visible spectrum at its absorption maximum $\lambda_{max}$=578 nm.

Example 9

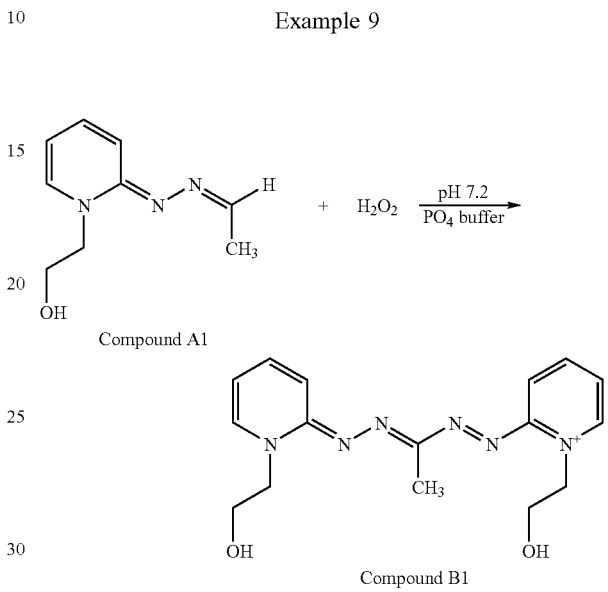

Compound A1

Compound B1

10 mg of azine (product A1) were dissolved in 5 ml of phosphate buffer (0.2M; pH 7.2). 0.57 ml of 5 volume strength hydrogen peroxide was added.

This mixture was applied to a lock of 0.5 g of hair containing 90% white hairs. After 30 minutes of contact, the lock of hair was rinsed, shampooed, rinsed and dried. The lock obtained was dyed blue.

Example 10

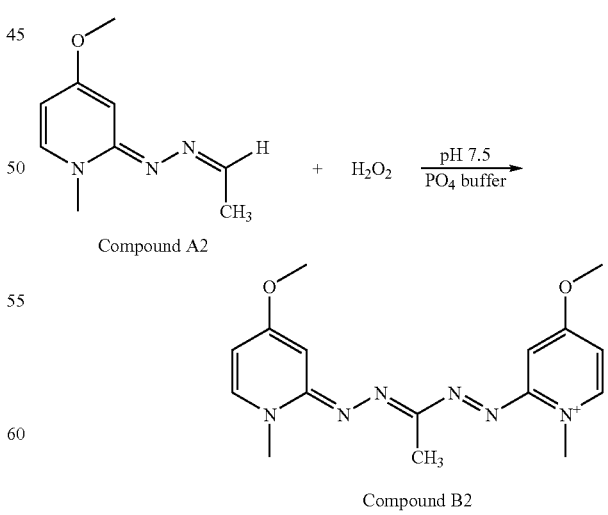

Compound A2

Compound B2

100 mg of azine (product A2) were dissolved in 5 ml of phosphate buffer (0.2M; pH 7.5). 0.57 ml of 5 volume strength hydrogen peroxide were added.

This mixture was applied to a lock of 0.5 g of hair containing 90% white hairs. After 30 minutes of contact, the lock of hair was rinsed, shampooed, rinsed and dried. The lock obtained was dyed violet.

Example 11

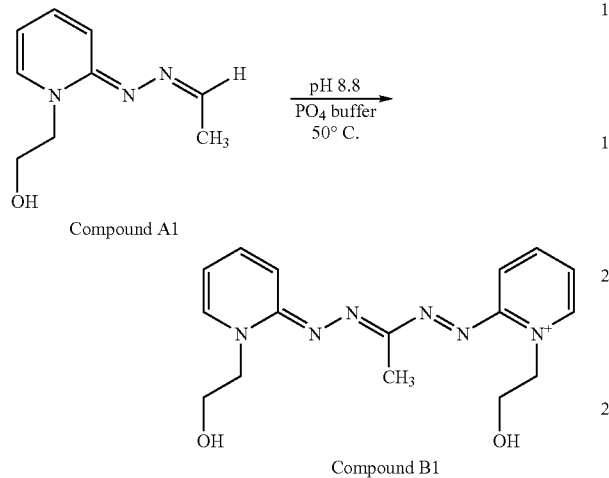

10 mg of azine (compound A1) were weighed out into 2.5 ml of phosphate buffer (0.2M; pH 8.8).

This mixture was applied to a lock of 0.25 g of natural hair containing 90% white hairs. After 30 minutes of contact at 50° C., the lock of hair was rinsed, shampooed, rinsed and dried. The lock obtained was dyed green-blue.

Example 12

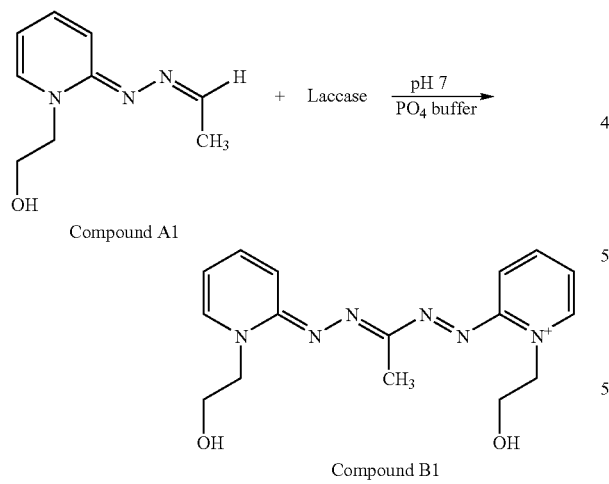

10 mg of azine (compound A1) were weighed out in 2.5 ml of phosphate buffer (0.2M; pH 7). 50 U of laccase enzyme were added.

This mixture was applied to a lock of 0.25 g of natural hair containing 90% white hairs. After 20 minutes of contact at room temperature, the lock of hair was rinsed, shampooed, rinsed and dried. The lock obtained was dyed blue.

Example 13

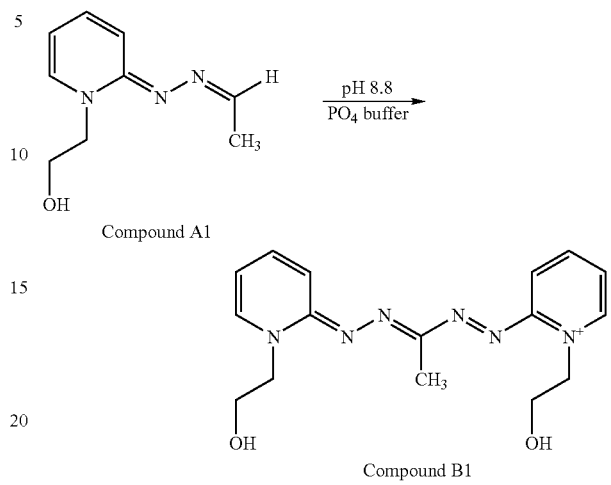

10 mg of azine (compound A1) were weighed out in 2.5 ml of phosphate buffer (0.2M; pH 8.8).

This mixture was applied to a lock of 0.25 g of natural hair containing 90% white hairs. After 90 minutes of contact at room temperature, the lock of hair was rinsed, shampooed, rinsed and dried. The lock obtained was slightly dyed green.

What is claimed is:

1. A process for dyeing keratin fibers comprising applying to wet or dry fibers, in the presence of at least one oxidizing agent, a dye composition comprising an azine compound of formula (VI) and/or (VII):

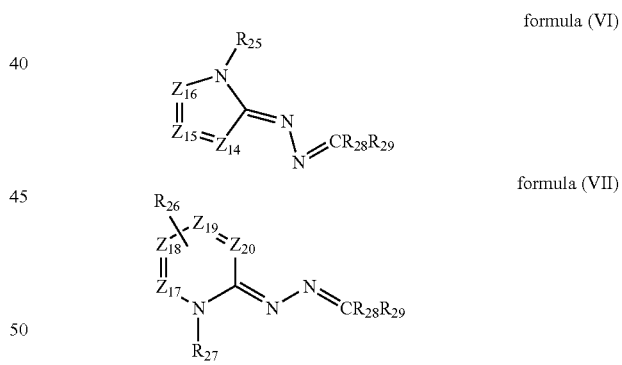

wherein:
  $Z_{14}$ is chosen from oxygen, sulfur, $NR_9$ radicals, and $NR_{15}$ radicals;
  $Z_{15}$ is chosen from nitrogen, $CR_{10}$ radicals, and $CR_{16}$ radicals;
  $Z_{16}$ is chosen from $CR_2$ radicals, $CR_6$ radicals, nitrogen, $NR_{21}$ radicals, and $NR_{22}$ radicals;
  $R_{25}$ is a linear or branched $C_1$-$C_8$ alkyl radical that is unsubstituted or substituted with one to three substituents chosen from hydroxyl, $C_1$-$C_2$ alkoxy, $C_2$-$C_4$ (poly) hydroxyalkoxy, amino, $C_1$-$C_2$ (di)alkylamino, carboxyl and sulfonic radicals;
  $Z_{17}$ is chosen from nitrogen, $CR_{11}$ radicals, and $CR_{17}$ radicals;

$Z_{18}$ is chosen from nitrogen, $CR_{12}$ radicals, and $CR_{18}$ radicals;

$Z_{19}$ is chosen from nitrogen, $CR_{13}$ radicals, and $CR_{19}$ radicals;

$Z_{20}$ is chosen from nitrogen, $CR_{14}$ radicals, and $CR_{20}$ radicals;

$R_{26}$ is chosen from hydrogen; linear and branched $C_1$-$C_{16}$ hydrocarbon-based chains, wherein the chains are optionally saturated or unsaturated with one to three unsaturations, wherein the chains are unsubstituted or substituted with one to three substituents chosen from hydroxyl, $C_1$-$C_2$ alkoxy, $C_2$-$C_4$ (poly)hydroxyalkoxy, amino, $C_1$-$C_2$ (di)alkylamino, carboxyl, sulfonic, sulfonylamino and $C_2$-$C_4$ (poly)hydroxyalkylamino radicals, and halogen atoms, and wherein the chains may be interrupted by one or two oxygen, nitrogen, or sulfur atoms, or by $SO_2$ radicals; phenyl radicals that are unsubstituted or substituted with one to three substituents chosen from hydroxyl, $C_1$-$C_2$ alkoxy, $C_2$-$C_4$ (poly)hydroxyalkoxy, amino, $C_1$-$C_2$ (di)alkylamino, carboxyl, sulfonic, sulfonylamino and $C_2$-$C_4$ (poly)hydroxy-alkylamino radicals, and halogen atoms; and heteroaryl radicals chosen from pyrazolyl, pyrrolyl, imidazolyl, thiazolyl, oxazolyl, triazolyl, pyridyl, pyrimidinyl, triazinyl, pyrazinyl and pyridazinyl radicals;

$R_{27}$ is a linear or branched $C_1$-$C_8$ alkyl radical that is unsubstituted or substituted with one to three substituents chosen from hydroxyl, $C_1$-$C_2$ alkoxy, $C_2$-$C_4$ (poly)hydroxyalkoxy, amino, $C_1$-$C_2$ (di)alkylamino, carboxyl and sulfonic radicals;

$R_{28}$ and $R_{29}$, which may be identical or different, are chosen from hydrogen; $C_1$-$C_6$ alkyl radicals; and linear and branched $C_1$-$C_6$ alkoxy radicals, wherein $R_{28}$ and $R_{29}$ are chosen such that at least one of the two radicals is not hydrogen;

and leaving the dye composition to act on the fibers for a period of time sufficient to develop the desired coloration.

2. The process according to claim 1, wherein $R_{28}$ and $R_{29}$ are chosen from $C_1$-$C_4$ alkyl radicals.

3. The process according to claim 1, wherein $R_{28}$ and $R_{29}$ are chosen from $C_1$-$C_4$ alkoxy radicals.

4. The process according to claim 1, wherein the keratin fibers are human keratin fibers.

5. The process according to claim 1, wherein the halogen atoms are chosen from chlorine, fluorine and bromine.

6. The process according to claim 1, further comprising mixing the at least one oxidizing agent with the dye composition at the time of use.

7. The process according to claim 1, further comprising applying the at least one oxidizing agent to the fibers simultaneously with the dye composition.

8. The process according to claim 1, further comprising applying the at least one oxidizing agent to the fibers sequentially to the dye composition.

9. The process according to claim 1, wherein the composition comprises compounds of formula (VI) and/or (VII) in an amount ranging from 0.001% to 10% by weight, relative to the total weight of the composition.

10. The process according to claim 1, wherein the composition comprises compounds of formula (VI) and/or (VII) in an amount ranging from 0.05% to 5% by weight, relative to the total weight of the dye composition.

11. The process according to claim 1, wherein the composition comprises at least one oxidation base and optionally at least one coupler, and/or at least one direct dye.

12. The process according to claim 1, wherein the composition comprises at least one oxidation base chosen from para-phenylenediamines, bis(phenyl)alkylenediamines, para-aminophenols, ortho-aminophenols, heterocyclic bases, and the addition salts thereof.

13. The process according to claim 12, wherein the at least one oxidation base is present in an amount ranging from 0.001% to 10% by weight, relative to the total weight of the dye composition.

14. The process according to claim 1, wherein the composition comprises at least one coupler chosen from meta-phenylenediamines, meta-aminophenols, meta-diphenols, naphthalene-based couplers, heterocyclic couplers, and the addition salts thereof.

15. The process according to claim 14, wherein the at least one coupler is present in an amount ranging from 0.001% to 10% by weight, relative to the total weight of the dye composition.

16. The process according to claim 1, wherein the composition comprises at least one direct dye.

17. The process according to claim 16, wherein the at least one direct dye is present in an amount ranging from 0.001% to 20% by weight, relative to the total weight of the dye composition.

* * * * *